US006924118B2

(12) United States Patent
Horwitz et al.

(10) Patent No.: US 6,924,118 B2
(45) Date of Patent: Aug. 2, 2005

(54) RECOMBINANT INTRACELLULAR PATHOGEN IMMUNOGENIC COMPOSITIONS AND METHODS FOR USE

(75) Inventors: Marcus A. Horwitz, Los Angeles, CA (US); Gunter Harth, Los Angeles, CA (US); Michael V. Tullius, Encino, CA (US)

(73) Assignee: The Regents of the University of California, Oakland, CA (US)

( * ) Notice: Subject to any disclaimer, the term of this patent is extended or adjusted under 35 U.S.C. 154(b) by 41 days.

(21) Appl. No.: 10/439,611

(22) Filed: May 15, 2003

(65) Prior Publication Data

US 2004/0009184 A1 Jan. 15, 2004

Related U.S. Application Data

(63) Continuation-in-part of application No. 10/261,981, filed on Sep. 30, 2002, now abandoned, which is a continuation-in-part of application No. 09/550,468, filed on Apr. 17, 2000, now Pat. No. 6,471,967.

(51) Int. Cl.[7] ........................ A61K 39/04; A61K 39/02; A61K 39/00; A61K 39/38

(52) U.S. Cl. ...................... 435/9.1; 435/9.2; 435/184.1; 435/185.1; 435/192.1; 435/200.1; 435/234.1; 435/248.1; 435/320.1

(58) Field of Search ....................... 424/9.1, 9.2, 184.1, 424/185.1, 192.1, 200.1, 234.1, 248.1; 435/320.1

(56) References Cited

U.S. PATENT DOCUMENTS

| | | | | |
|---|---|---|---|---|
| 5,504,005 | A | 4/1996 | Bloom et al. | 435/472 |
| 5,583,038 | A | 12/1996 | Stover | 435/252.3 |
| 5,591,632 | A | 1/1997 | O'Donnell et al. | 435/252.3 |
| 5,679,515 | A | 10/1997 | Stover et al. | 435/6 |
| 5,700,683 | A | 12/1997 | Stover et al. | 435/252.31 |
| 5,736,367 | A | 4/1998 | Haun et al. | 435/252.3 |
| 5,776,465 | A | 7/1998 | O'Donnell et al. | 424/200.1 |
| 5,807,723 | A | 9/1998 | Aldovini et al. | 435/477 |
| 5,830,475 | A | 11/1998 | Aldovini et al. | 424/200.1 |
| 5,854,055 | A | 12/1998 | Bloom et al. | 435/253.1 |
| 5,866,403 | A | 2/1999 | Aldovini et al. | 435/252.3 |
| 5,869,057 | A | 2/1999 | Rock | 424/192.1 |
| 6,015,696 | A | 1/2000 | Yamada et al. | 435/69.8 |

FOREIGN PATENT DOCUMENTS

| | | | |
|---|---|---|---|
| WO | WO 88/06626 | 9/1988 | C12N/15/00 |
| WO | PCT/US03/30994 | 5/2004 | |

OTHER PUBLICATIONS

Cirillo et al., "Bacterial Vaccine Vectors and Bacillus Calmette–Guerin," Clinical Infectious Diseases, 20:1001–9 (1995).

Fuerst et al., "Development and Analysis of Recombinant BCG Vector Systems," AIDS Research and Human Retroviruses, vol. 8 (1992).

Hanson, et al., "Efficacy and Safety of Live Recombinant BCG Vaccines,"Dev. Biol. Stand. Basel, Karger, 84:229–36 (1995).

Harth et al., "High–Level Hetrologous Expression and Secretion in Rapidly Growing Nonpathogenic Mycobacteria of Four Major Mycobacterium Tuberculosis Extracellular Proteins Considered to be Leading Vaccine Candidates and Drug Targets," Infection and Immunity, 65:2321–8 (Jun. 1997).

Harth et al., "Novel Insights Into the Genetics, Biochemistry, and Immunocytochemistry of the 30–Kilodalton Major Extracellular Protein of Mycobacterium Tuberculosis," Infection and Immunity 64:3038–47 (Aug. 1996).

Horwitz et al., "Recombinant Bacillus Calmette–Guerin (BCG) Vaccines Expressing the Mycobacterium Tuberculosis 20–kDa Major Secretory Protein Induce Greater Protective Immunity Against Tuberculosis Than Conventional BCG Vaccines in a Highly Susceptible Animal Model," PNAS 97:13853–8 (Dec. 2000).

Langermann et al., "Protective Humoral Response Against Pneumococcal Infection in Mice Elicited by Recombinant Bacille Calmette–Guerin Vaccines Expressing Pneumococcal Surface Protein A," J. Exp. Med., The Rockeffeller University Press, 180:2277–86 (Dec. 1994).

Langermann et al., "Systemic and Mucosal Immunity Induced by BCG Vector Expressing Outer–Surface Protein A of *Borrelia burgdorferi*," Nature, vol. 372 (Dec. 1994).

Lee et al., "T–Cell Epitope Mapping of the Three Most Abundant Extracellular Proteins of Mycobacterium Tuberculosis in Outbread Guinea Pigs," Infection and Immunity, 67:2665–70 (May 1999).

Naito et al., "The Antigen 85 Complex Vaccine Against Experimental Mycobacterium Leprae Infection in Mice," Vaccine 19:795–8 (2000).

Ohara et al., "Characterization of the Transcriptional Initiation Regions of Genes for the Major Secreted Protein Antigens 85C and MPB51 of Mycobacterium Bovis BCG," Vaccine 19:1294–7 (2000).

Ohara et al., "Inhibition of Multiplication of Mycobacterium Laprae in Mouse Foot Pads by Recombinant Bacillus Catmette–Guerin (BCG)," Vaccine, 19:1294–7 (2000).

(Continued)

*Primary Examiner*—Rodney P. Swartz

(74) *Attorney, Agent, or Firm*—Louis C. Cullman; Michelle S. Glasky; Preston Gates & Ellis LLP

(57) ABSTRACT

Immunogenic compositions comprising recombinant attenuated intracellular pathogens that have been transformed to express recombinant immunogenic antigens of the same or other intracellular pathogens are provided. Exemplary immunogenic compositions include, but are not limited to attenuated recombinant *Mycobacteria* expressing the major extracellular non-fusion proteins of *Mycobacteria* and/or other intracellular pathogens. Other embodiments are provided wherein the recombinant attenuated intracellular pathogen is auxotrophic.

34 Claims, 6 Drawing Sheets

OTHER PUBLICATIONS

Stover et al., "New Use of BCG for Recombinant Vaccines," Nature, vol. 351 (Jun. 1991).

Stover et al., "Protective Immunity Elicited by rBCG Vaccines," Brown (ed) "Recombinant Vectors in Vaccine Development," Dev. Biol. Stand., Basel, Karger, 82:163–70 (1994).

Stover et al., "Protective Immunity Elicited by Recombinant Bacille Calmette–Guerin (BCG) Expressing Outer Surface Protein A (OspA) Lipoprotein: A Candidate Lyme Disease Vaccine," J. Exp. Med., The Rockefeller University Press, 178:197–209 (1993).

Stover et al., "Use of Recombinant BCG as a Vaccine Delivery Vehicle," Advances in Experimental Medicine and Biology, vol. 327 (date).

Yasutomi et al., "Immunization with Recombinant BCG–SIV Elicits SIV–Specific Cytotoxic T. Lymphocytes in Rhesus Monkeys," The Journal of Immunology, 150:3101–7 (Apr. 1993).

SECRETION OF *M. TUBERCULOSIS* 30 kDa MAJOR EXTRACELLULAR PROTEIN BY BCG

1, COOMASSIE STAINED PROTEINS AFTER 4 WEEKS OF GROWTH IN BROTH CULTURE

2, IMMUNOBLOT WITH ANTI-30 kDA PROTEIN IgG AFTER 4 WEEKS OF GROWTH IN BROTH CULTURE

3, IMMUNOBLOT WITH ANTI-30 kDa PROTEIN IgG AFTER 12 WEEKS OF GROWTH IN BROTH CULTURE WITHOUT HYGROMYCIN

RECOMBINANT INTRACELLULAR PATHOGEN IMMUNOGENIC COMPOSITIONS AND METHODS FOR USE

RELATED APPLICATIONS

This application is a continuation-in-part of application Ser. No. 10/261,981 filed Sep. 30, 2002, now abandoned, which is a continuation-in-part of application Ser. No. 09/550,468 filed Apr. 17, 2000, now U.S. Pat. No. 6,471, 967.

REFERENCE TO GOVERNMENT

This invention was made with Government support under Grant No. AI31338 awarded by the Department of Health and Human Services. The Government has certain rights in this invention.

FIELD OF THE INVENTION

The present invention generally relates to immunogenic compositions derived from recombinant attenuated intracellular pathogenic bacteria. More specifically, the present invention relates to immunogenic compositions comprising recombinant attenuated *Mycobacteria* that over-express and secrete major extracellular proteins. Moreover, the immunogenic compositions of the present invention also comprise recombinant attenuated *Mycobacteria* including auxotrophic strains. The immunogenic compositions of the present invention are useful in inducing immune responses in hosts.

BACKGROUND OF THE INVENTION

It has long been recognized that parasitic microorganisms possess the ability to infect animals thereby causing disease and often death. Pathogenic agents have been a leading cause of death throughout history and continue to inflict immense suffering. Though the last hundred years have seen dramatic advances in the prevention and treatment of many infectious diseases, complicated host-parasite interactions still limit the universal effectiveness of therapeutic measures. Difficulties in countering the sophisticated invasive mechanisms displayed by many pathogenic organisms is evidenced by the resurgence of various diseases such as tuberculosis, as well as the appearance of numerous drug resistant strains of bacteria and viruses.

Among those pathogenic agents of major epidemiological concern, intracellular bacteria have proven to be particularly intractable in the face of therapeutic or prophylactic measures. Intracellular bacteria, including the genus *Mycobacterium*, complete all or part of their lifecycle within the cells of the infected host organism rather than extracellularly. Around the world, intracellular bacteria are responsible untold suffering and millions of deaths each year. Tuberculosis is the leading cause of death from a single disease agent worldwide, with 10 million new cases and 2.9 million deaths annually. In addition, intracellular bacteria are responsible for millions of cases of leprosy. Other debilitating diseases transmitted by intracellular agents include cutaneous and visceral leishmaniasis, American trypanosomiasis (Chagas disease), listeriosis, toxoplasmosis, histoplasmosis, trachoma, psittacosis, Q-fever, and legionellosis.

Currently it is believed that approximately one-third of the world's population is infected by *M. tuberculosis* resulting in millions of cases of pulmonary tuberculosis annually. More specifically, human pulmonary tuberculosis primarily caused by *M. tuberculosis* is a major cause of death in developing countries. Capable of surviving inside macrophages and monocytes, *M. tuberculosis* may produce a chronic intracellular infection. *M. tuberculosis* is relatively successful in evading the normal defenses of the host organism by concealing itself within the cells primarily responsible for the detection of foreign elements and subsequent activation of the immune system. Moreover, many of the front-line chemotherapeutic agents used to treat tuberculosis have relatively low activity against intracellular organisms as compared to extracellular forms. These same pathogenic characteristics have heretofore limited the effectiveness of immunotherapeutic agents or immunogenic compositions against tubercular infections.

Recently, tuberculosis resistance to one or more drugs was reported in 36 of the 50 United States. In New York City, one-third of all cases tested was resistant to one or more major drugs. Though non-resistant tuberculosis can be cured with a long course of antibiotics, the outlook regarding drug resistant strains is bleak. Patients infected with strains resistant to two or more major antibiotics have a fatality rate of around 50%. Accordingly, safe and effective immunogenic compositions against such varieties of *M. tuberculosis* are sorely needed.

Initial infections of *M. tuberculosis* almost always occur through the inhalation of aerosolized particles as the pathogen can remain viable for weeks or months in moist or dry sputum. Although the primary site of the infection is in the lungs, the organism can also cause infection of nearly any organ including, but not limited to, the bones, spleen, kidney, meninges and skin. Depending on the virulence of the particular strain and the resistance of the host, the infection and corresponding damage to the tissue may be minor or extensive. In the case of humans, the initial infection is controlled in the majority of individuals exposed to virulent strains of the bacteria. The development of acquired immunity following the initial challenge reduces bacterial proliferation thereby allowing lesions to heal and leaving the subject largely asymptomatic.

When *M. tuberculosis* is not controlled by the infected subject it often results in the extensive degradation of lung tissue. In susceptible individuals lesions are usually formed in the lung as the tubercle bacilli reproduce within alveolar or pulmonary macrophages. As the organisms multiply, they may spread through the lymphatic system to distal lymph nodes and through the blood stream to the lung apices, bone marrow, kidney and meninges surrounding the brain. Primarily as the result of cell-mediated hypersensitivity responses, characteristic granulomatous lesions or tubercles are produced in proportion to the severity of the infection. These lesions consist of epithelioid cells bordered by monocytes, lymphocytes and fibroblasts. In most instances a lesion or tubercle eventually becomes necrotic and undergoes caseation (conversion of affected tissues into a soft cheesy substance).

While *M. tuberculosis* is a significant pathogen, other species of the genus *Mycobacterium* also cause disease in animals including man and are clearly within the scope of the present invention. For example, *M. bovis* is closely related to *M. tuberculosis* and is responsible for tubercular infections in domestic animals such as cattle, pigs, sheep, horses, dogs and cats. Further, *M. bovis* may infect humans via the intestinal tract, typically from the ingestion of raw milk. The localized intestinal infection eventually spreads to the respiratory tract and is followed shortly by the classic symptoms of tuberculosis. Another important pathogenic vector of the genus *Mycobacterium* is *M. leprae* that causes millions of cases of the ancient disease leprosy. Other species of this genus which cause disease in animals and man include *M. kansasii, M. avium intracellulare, M. fortuitum, M. marinum, M. chelonei,* and *M. scrofulaceum.* The pathogenic mycobacterial species frequently exhibit a high degree of homology in their respective DNA and corresponding protein sequences and some species, such as *M. tuberculosis* and *M. bovis*, are highly related.

For obvious practical and moral reasons, initial work in humans to determine the efficacy of experimental compositions with regard to such afflictions is infeasible. Accordingly, in the early development of any drug or immunogenic composition it is standard procedure to employ appropriate animal models for reasons of safety and expense. The success of implementing laboratory animal models is predicated on the understanding that immunogenic epitopes are frequently active in different host species. Thus, an immunogenic determinant in one species, for example a rodent or guinea pig, will generally be immunoreactive in a different species such as in humans. Only after the appropriate animal models are sufficiently developed will clinical trials in humans be carried out to further demonstrate the safety and efficacy of a immunogenic composition in man.

With regard to alveolar or pulmonary infections by *M. tuberculosis*, the guinea pig model closely resembles the human pathology of the disease in many respects. Accordingly, it is well understood by those skilled in the art that it is appropriate to extrapolate the guinea pig model of this disease to humans and other mammals. As with humans, guinea pigs are susceptible to tubercular infection with low doses of the aerosolized human pathogen *M. tuberculosis*. Unlike humans where the initial infection is usually controlled, guinea pigs consistently develop disseminated disease upon exposure to the aerosolized pathogen, facilitating subsequent analysis. Further, both guinea pigs and humans display cutaneous delayed-type hypersensitivity reactions characterized by the development of a dense mononuclear cell induration or rigid area at the skin test site. Finally, the characteristic tubercular lesions of humans and guinea pigs exhibit similar morphology including the presence of Langhans giant cells. As guinea pigs are more susceptible to initial infection and progression of the disease than humans, any protection conferred in experiments using this animal model provides a strong indication that the same protective immunity may be generated in man or other less susceptible mammals. Accordingly, for purposes of explanation only and not for purposes of limitation, the present invention will be primarily demonstrated in the exemplary context of guinea pigs as the mammalian host. Those skilled in the art will appreciate that the present invention may be practiced with other mammalian hosts including humans and domesticated animals.

Attempts to eradicate tuberculosis using immunogenic compositions was initiated in 1921 after Calmette and Guérin successfully attenuated a virulent strain of *M. bovis* at the Institut Pasteur in Lille, France. This attenuated *M. bovis* became known as the Bacille Calmette Guérin, or BCG for short. Nearly eighty years later, immunogenic compositions derived from BGC remain the only prophylactic therapy for tuberculosis currently in use. In fact, all BCG immunogenic compositions available today are derived from the original strain of *M. bovis* developed by Calmette and Guérin at the Institut Pasteur.

The World Health Organization considers the BCG immunogenic compositions an essential factor in reducing tuberculosis worldwide, especially in developing nations. In theory, BCG immunogenic composition confers cell-mediated immunity against an attenuated mycobacterium that is immunologically related to *M. tuberculosis*. The resulting immune response should inhibit primary tuberculosis. Thus, if primary tuberculosis is inhibited, latent infections cannot occur and disease reactivation is avoided.

Current BCG immunogenic compositions are provided as lyphophilzed cultures that are re-hydrated with sterile diluent immediately before administration. The BCG immunogenic composition is given at birth, in infancy, or in early childhood in countries that practice BCG vaccination, including developing and developed countries. Adult visitors to endemic regions who may have been exposed to high doses of infectious mycobacteria may receive BCG as a prophylactic providing they are skin test non-reactive. Adverse reactions to the immunogenic composition are rare and are generally limited to skin ulcerations and lymphadenitis near the injection site. However, in spite of these rare adverse reactions, the BCG immunogenic composition has an unparalleled history of safety with over three billion doses having been administered worldwide since 1930.

However, the unparalleled safety of traditional BCG immunogenic compositions is coming under increased scrutiny and has created a paradox for healthcare practitioners. The population segments most susceptible to mycobacterial infections are the immunosuppressed. Persons suffering from early or late-sage HIV infections are particularly susceptible to infection. Unfortunately, many persons in the early-stage of HIV infection are unaware of their immune status. It is likely that these individuals may voluntarily undergo immunization using a live attenuated immunogenic composition such as BCG without being forewarned of their unique risks. Moreover, other mildly immunosuppressed individuals may also unwittingly undergo immunization with BCG hoping to avoid mycobacterial disease. Therefore, safer, more efficacious BCG and BCG-like immunogenic compositions are desirable.

Recently, significant attention has been focused on using transformed BCG strains to produce immunogenic compositions that express various cell-associated antigens. For example, C. K. Stover, et al. have reported a Lyme Disease immunogenic composition using a recombinant BCG (rBCG) that expresses the membrane associated lipoprotein OspA of *Borrelia burgdorferi*. Similarly, the same author has also produced a rBCG immunogenic composition expressing a pneumococcal surface protein (PsPA) of *Streptococcus pneumoniae*. (Stover, C. K., G. P. Bansal, S. Langerman, and M. S. Hanson. 1994. Protective Immunity Elicited by rBCG Immunogenic compositions. In: Brown F. (ed): Recombinant Vectors in Immunogenic composition Development. Dev Biol Stand. Dasel, Karger, Vol. 82, 163–170.)

U.S. Pat. No. (USPN) 5,504,005 (the "'005" patent") and U.S. Pat. No. 5,854,055 (the "'055 patent") both issued to B. R. Bloom et al., disclose theoretical rBCG vectors expressing a wide range of cell associated fusion proteins from numerous species of microorganisms. The theoretical vectors described in these patents are either directed to cell associated fusion proteins, as opposed to extracellular non-fusion protein antigens, and/or the rBCG is hypothetically expressing fusion proteins from distantly related species. Moreover, the recombinant cell associated fusion proteins expressed in these models are encoded on DNA that is integrated into the host genome and under the control of heat shock promoters. Consequently, the antigens expressed are fusion proteins and expression is limited to levels approximately equal to, or less than, the vector's native proteins.

Furthermore, neither the '005 nor the '055 patent disclose animal model safety testing, immune response development or protective immunity in an animal system that closely emulates human disease. In addition, only theoretical rBCG vectors expressing *M. tuberculosis* fusion proteins are disclosed in the '005 and '055, no actual immunogenic compositions are enabled. Those immunogenic composition models for *M. tuberculosis* that are disclosed are directed to cell associated heat shock fusion proteins, not extracellular non-fusion proteins.

U.S. Pat. No. 5,830,475 (the "'475 patent") also discloses theoretical mycobactenal immunogenic compositions used to express fusion proteins. The DNA encoding for these fusion proteins resides in extrachromosomal plasmids under the control of mycobacterial heat shock protein and stress protein promoters. The immunogenic compositions disclosed are intended to elicit immune responses in non-human animals for the purpose of producing antibodies thereto and not shown to prevent intracellular pathogen diseases in mammals. Moreover, the '475 patent does not disclose recombinant immunogenic compositions that use protein specific promoters to express extracellular non-fusion proteins.

U.S. Pat. No. 6,467,967 issued to the present inventor, claims immunogenic compositions comprising a recombinant BCG having an extrachromosomal nucleic acid sequence comprising a gene encoding for a *M. tuberculosis* 30 kDa major extracellular protein, wherein said *M. tuberculosis* 30 kDa major extracellular protein is over expressed and secreted. Moreover, the present inventors have filed a continuation-in-part (U.S. patent application Ser. No. 10/261981 filed Sep. 30, 2002) claiming additionally a recombinant BCG that over expresses other *M. tuberculosis* major extracellular proteins.

Therefore, there remains a need for recombinant intracellular pathogen immunogenic compositions that express major extracellular non-fusion proteins of intracellular pathogens that are closely related to the immunogenic composition. Furthermore, there is a need for recombinant intracellular pathogen immunogenic compositions that are capable of over-expressing recombinant extracellular non-fusion proteins by virtue of extrachromosomal DNA having non-heat shock gene promoters or non-stress protein gene promoters.

Specifically, there remains an urgent need to produce intracellular pathogen immunogenic compositions that provide recipients protection from diseases that is superior to the protection afforded BCG immunogenic composition recipients. Moreover, there is an urgent need to provide both developed and developing countries with a cost efficient, immunotherapeutic and prophylactic treatment for tuberculosis and other intracellular pathogens.

Additionally, there remains a need for intracellular pathogen immunogenic compositions that can be safely administered to immunosuppressed, or partially immunosuppressed individuals.

Therefore, it is an object of the present invention to provide immunogenic compositions for the diagnosis, treatment, prevention, inhibition or palliation of disease caused by intracellular pathogens.

It is another object of the present invention to provide immunogenic compositions for the diagnosis, treatment, prevention, inhibition or palliation of disease caused by intracellular pathogens using intracellular pathogens that have been transformed to express the major recombinant immunogenic antigens of the same intracellular pathogen, another intracellular pathogen, or both.

It is yet another object of the present invention to provide immunogenic compositions for the diagnosis, treatment, prevention, inhibition or palliation of disease caused by mycobacteria diseases using recombinant BCG that expresses the extracellular protein(s) of a pathogenic mycobacterium.

It is another object of the present invention to provide immunogenic compositions for the diagnosis, treatment, prevention, inhibition or palliation of tuberculosis using recombinant strains of BCG that express and secrete one or more major extracellular proteins of *Mycobacterium tuberculosis.*

It is yet another object of the present invention to provide the aforementioned immunogenic compositions in a form that can be safely administered to immunosuppressed, or partially immunosuppressed individuals.

SUMMARY OF THE INVENTION

The present invention accomplishes the above-described and other objects by providing a new class of immunogenic compositions and immunotherapeutics and methods for the diagnosis, treatment, prevention, inhibition or palliation of intracellular pathogen diseases in mammals. Historically intracellular pathogen immunogenic compositions and immunotherapeutics have been prepared from the intracellular pathogen itself or a closely related species. These old immunogenic composition models were composed of the entire microorganism or subunits thereof. For example, the first, and currently only available immunogenic composition, for *Mycobacterium tuberculosis* is an attenuated live immunogenic composition made from the closely related intracellular pathogen *M. bovis*. Recently, the present inventors have discovered that specific extracellular products of intracellular pathogens that are secreted into growth media can be used to illicit potent immune responses in mammals either as individual subunits, or in subunit combinations. However, these subunit immunogenic compositions have not proven to be superior to the original attenuated immunogenic composition derived from *M. bovis.*

The present invention details immunogenic compositions and immunotherapeutics composed of recombinant attenuated intracellular pathogens that have been transformed to express the extracellular protein(s) (recombinant immunogenic antigens) of another or same intracellular pathogen. In one embodiment the immunogenic compositions of the present invention are made using recombinant strains of the Bacille Calmette and Guérin, or BCG. In this embodiment the recombinant BCG expresses major extracellular proteins of pathogenic mycobacteria including, but not limited to, *M. tuberculosis, M. leprae* and *M. bovis*, to name but a few.

The major extracellular proteins expressed by the recombinant BCG include, but are not limited to, the 12 kDa, 14 kDa, 16 kDa, 23 kDa, 23.5 kDa, 30 kDa, 32A kDa, 32B kDa, 45 kDa, 58 kDa, 71 kDa, 80 kDa, and 110 kDa of *Mycobacterium* sp. and respective analogs, homologs and subunits thereof including recombinant non-fusion proteins, fusion proteins and derivatives thereof. It is apparent to those of ordinary skill in the art that the molecular weights used to identify the major extracellular proteins of Mycobactena and other intracellular pathogens are only intended to be approximations. Those skilled in the art of recombinant technology and molecular biology will realize that it is possible to co-express (co-translate) these proteins with additional amino acids, polypeptides and proteins, as it is also possible to express these proteins in truncated forms. The resulting modified proteins are still considered to be within the scope of the present invention whether termed native, non-fusion proteins, fusion proteins, hybrid proteins or chimeric proteins. For the purposes of the present invention, fusion proteins are defined to include, but not limited to, the products of two or more coding sequences from different genes that have been cloned together and that, after translation, form a single polypeptide sequence.

The present invention also describes recombinant attenuated intracellular pathogen immunogenic compositions that over express non-fusion proteins from at least one other intracellular pathogen. This is accomplished by using extrachromosomal nucleic acids to express at least one recombinant immunogenic antigen gene and placing this gene(s) under the control of non-heat shock gene promoters or non-stress protein gene promoters, preferably protein-specific promoter sequences. Consequently, immunogenic compositions are provided having non-fusion, recombinant immunogenic antigens expressed in greater quantities than possible when genes encoding for recombinant immunogenic antigens are stably integrated into the immunogenic composition's genomic DNA. As a result, intracellular pathogen immunogenic compositions having surprisingly superior specificity and potency than existing subunit or attenuated intracellular pathogen immunogenic compositions are provided.

Moreover the present invention describes methods of treating and preventing mammalian diseases caused by intracellular pathogens using the immunogenic compositions of the present invention. A partial list of the many intracellular pathogens that may be used as the attenuated organism and/or the source of the recombinant immunogenic antigens includes, but is not limited to, *Mycobacterium bovis, M. tuberculosis, M. leprae, M. kansasii, M. avium, Mycobacterium* sp., *Legionella pneumophila, L. longbeachae, L. bozemanii, Legionella* sp., *Rickettsia rickettsii, Rickettsia typhi, Rickettsia* sp., *Ehrlichia chaffeensis, Ehrlichia phagocytophila* geno group, *Ehrlichia* sp., *Coxiella burnetii, Leishmania* sp, *Toxpolasma gondii, Trypanosoma cruzi, Chlamydia pneumoniae, Chiamydia* sp, *Listeria monocytogenes, Listeria* sp, and *Histoplasma* sp.

It is understood that the immunogenic compositions of the present invention may be administered using any approach that will result in the appropriate immune response including, but not limited to, intradermal subcutaneous, intramuscular, intranasal, intraperitoneal, oral, or inhalation. Following a suitable post inoculation period, the mammals were challenged with an infectious *M. tuberculosis* aerosol. Mammals receiving the immunogenic composition of the present invention were remarkably disease free as compared to mammals receiving BCG alone, the major extracellular protein alone, or any combinations thereof.

In one embodiment of the present invention an immunogenic composition comprising a recombinant BCG having an extrachromosomal nucleic acid sequence and a gene encoding for at least one Mycobacterial extracellular protein, wherein the Mycobacterial major extracellular protein is over expressed and secreted such that an immune response is induced in an animal is provided.

In another embodiment an immunogenic composition comprising a recombinant BCG having an extrachromosomal nucleic acid sequence comprising a gene encoding for *Mycobacterium tuberculosis* 23.5 kDa major extracellular non-fusion protein under the control of a promoter wherein the promoter is not a heat shock promoter or stress protein promoter and wherein the 23.5 kDa major extracellular non-fusion protein is over expressed and secreted such that an immune response is induced in an animal is provided.

In yet another embodiment of the present invention an immunogenic composition comprising a recombinant BCG having an extrachromosomal nucleic acid sequence comprising a gene encoding for *Mycobacterium tuberculosis* 32A kDa major extracellular non-fusion protein under the control of a promoter wherein the promoter is not a heat shock promoter or stress protein promoter and wherein the 32A kDa major extracellular non-fusion protein is over expressed and secreted such that an immune response is induced in an animal.

Another embodiment provides an immunogenic composition comprising a recombinant BCG having an extrachromosomal nucleic acid sequence comprising a genetic construct having at least one gene encoding for a *Mycobacteria tuberculosis* (Mtb) 30 kDa major extracellular protein and an Mtb 23.5 kDa major extracellular non-fusion protein, wherein the Mtb 30 kDa major extracellular protein and the Mtb 23.5 kDa major extracellular non-fusion protein are over expressed and secreted such that an immune response is induced in an animal.

In another exemplary embodiment an immunogenic composition comprising a recombinant BCG having an extrachromosomal nucleic acid comprising a gene encoding for *Mycobacterium bovis* 30 kDa major extracellular non-fusion protein under the control of a promoter wherein the promoter is not a heat shock promoter or stress protein promoter and wherein the *Mycobacterium bovis* 30 kDa major extracellular non-fusion protein is over expressed and secreted from said recombinant BCG such that both a humoral and a cellular immune response is induced in an animal is disclosed.

Yet another embodiment of the present invention disclosed is an immunogenic composition comprising a recombinant BCG having an extrachromosomal nucleic acid comprising a gene encoding for *Mycobacterium leprae* 30 kDa major extracellular non-fusion protein under the control of a promoter wherein said promoter is not a heat shock promoter or stress protein promoter and wherein the *Mycobacterium leprae* 30 kDa major extracellular non-fusion protein is over expressed and secreted from the recombinant BCG such that both a humoral and a cellular immune response is induced in an animal.

Other embodiments of the present invention include immunogenic compositions wherein the attenuated intracelluar pathogen (e.g. recombinant BCG) is a growth regulatable auxotrophic organism. As used herein "growth regulatable" refers to an auxotrophic organism that grows when provided with a specific nutrient. The specific nutrient is either co-administered with the immunogenic composition, or provided to the immunogenic composition recipient subsequently.

In one embodiment the growth regulatable auxotrophic organism is a recombinant BCG transformed to over express and secrete at least one major extracellular protein of *M. tuberculosis.*

In another embodiment of the present invention the specific nutrient required to regulate growth of the growth regulatable auxotrophic organism is an amino acid.

Another embodiment of the present invention includes an attenuated recombinant BCG (Tice strain) wherein the nitrate reductase alpha subunit gene (narG gene) was disrupted via allelic exchange. This highly attenuated narG BCG is then transformed with at least one heterologous nucleic acid encoding for at least one major extracellular Mtb protein. The resulting highly attenuated narG mutant transformant is useful as an immunogenic composition in immunosuppressed mammals.

Other objects and features and advantages of the present invention will be apparent to those skilled in the art from a consideration of the following detailed description of preferred exemplary embodiments thereof taken in conjunction with the Figures which will first be described briefly.

BRIEF DEFINITION OF TERMS

Figure 1A:
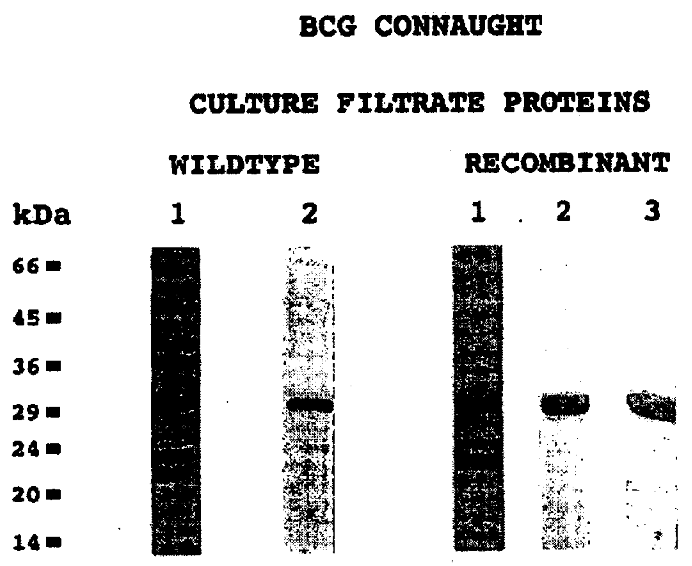
FIG. 1 depicts Coomassie blue stained gels labeled 1*a* and 1*b* illustrating the secretion of *Mycobacterium tuberculosis* recombinant 30 kDa by transformed strains of BCG from culture filtrates.

To facilitate an understanding of the following Detailed Description, Examples and appended claims it may be useful to refer to the following definitions. These definitions are non-limiting in nature and are supplied merely as a convenience to the reader.

Auxotroph or auxotrophic: As used herein "auxotroph" refers to a microorganism having a specific nutritional requirement NOT required by the wild-type organism. In the absence of the required nutrient the auxotroph will not growth whereas the wild-type will thrive.

Gene: A "gene" as used herein refers to a least a portion of a genetic construct having a promoter and/or other regulatory sequences required for, or that modify the expression of, the genetic construct.

Genetic Construct: A "genetic construct" as used herein shall mean a nucleic acid sequence encoding for at least one major extracellular protein from at least one extracellular pathogen. In one embodiment of the present invention the genetic construct is extrachromosomal DNA.

Growth Regulatable: As used herein the term "growth regulatable" refers to an auxotrophic form of the present invention's immunogenic compositions. Growth is regulated by administering a nutrient essential for the auxotroph's growth at a concentration sufficient to induce growth.

Host: As used herein "host" refers to the recipient of the present immunogenic compositions. Exemplary hosts are mammals including, but not limited to primates, rodents, cows, horses, dogs, cats, sheep, goats and pigs. In one embodiment of the present invention the host is a human.

Immunogen: As used herein the term "immunogen" shall mean any substrate that elicits an immune response in a host. Immunogens of the present invention include, but are not limited to major extracellular proteins, and their recombinant forms, derived from intracellular pathogens, such as, but not limited to members of the genus *Mycobacterium.*

Immunogenic Composition: An "immunogenic composition" as used herein comprises a recombinant vector, with or without an adjuvant, such as an intracellular pathogen, that expresses and/or secretes an immunogen in vivo wherein the immunogen elicits an immune response in the host. The immunogenic compositions disclosed herein may or may not include an auxotrophic organism as the transformant.

Nucleic Acid Sequence: As used herein the term "nucleic acid sequence" shall mean any continuous sequence of nucleic acids.

Transformant: As used herein a "transformant" refers to a microorganism that has been transformed with at least one heterologous nucleic acid encoding for a polypeptide that is expressed and/or secreted. In one embodiment of the present invention the transformant is BCG.

The present invention is directed generally to immunogenic compositions comprising attenuated, or avirulent, recombinant intracellular pathogens that express and/or secrete recombinant immunogenic antigens of the same, or another species. In another embodiment of the present invention the attenuated intracellular pathogen is growth regulatable auxotroph. In yet another embodiment of the present invention the attenuated intracellular pathogen is attenuated via allelic exchange. Exemplary embodiments of the present invention are based on attenuated or avirulent recombinant BCG. However, the present invention is not limited to recombinant BCG.

The immunogenic compositions are administered using one or more routes, including, but not limited to, subcutaneous, intramuscular, intranasal, intraperitoneal, intradermal, oral, or inhalation. The immunogenic compositions of the present invention survive within the host expressing and secreting the immunogen(s) in situ. When an auxotrophic strain is used the immunogenic composition remains essentially immunologically inert until a sufficient quantity of the appropriate nutrient is provided to the host. Once the essential nutrient is provided, the auxotrophic immunogenic composition (auxotroph) begins expressing and secreting the immunogen. Later, if desired, withholding the essential nutrient can halt the auxotroph's growth and antigen expression in situ.

The immunogenic compositions are administered using one or more routes, including, but not limited to, subcutaneous, intramuscular, intranasal, intraperitoneal, intradermal, oral, or inhalation. The immunogenic compositions of the present invention survive within the host expressing and secreting the immunogen(s) in situ. When an auxotrophic strain is used the immunogenic composition remains essentially immunologically inert until a sufficient quantity of the appropriate nutrient is provided to the host. Once the essential nutrient is provided, the auxotrophic immunogenic composition (auxotroph) begins expressing and secreting the immunogen. Later, if desired, withholding the essential nutrient can halt the auxotrph's growth and antigen expression in situ.

When the immunogenic compostions of the present invention utilize an auxotrophic transfomant expressing an immunogen, the essential nutrient required to initiate the auxotroph's growth within the host can be administered either immediately before, concurrent with or immediately after the immunogenic composition is administered. It is also within the scope of the present invention to delay administration of the essential nutrient days or even weeks following administration of the immunogenic composition. Furthermore, the essential nutrient can be withheld from the host at any time following administration of the immunogenic composition to stop proliferation of the auxotrophic transformant.

The present invention is useful for preparing immunogenic compositions against a variety of intracellular pathogens including, but not limited to BCG strains over-expressing the major extracellular non-fusion proteins of *M. tuberculosis, M. bovis* or *M. leprae*. Immunogenic compositions made in accordance with the teachings of the present invention are useful in eliciting immune responses in hosts. The induced immune responses can be either humoral (antibody-based) or cellular and are useful in diagnostic, protective, or palliative applications.

Each immunogenic composition of the present invention can express at least one immunogen of various molecular weights specific for a given intracellular pathogen. For example, the present inventors have previously identified *M. tuberculosis* immunogens that can include, but are not limited to, the major extracellular proteins 12 kDa, 14 kDa, 16 kDa, 23 kOa, 23.5 kDa, 30 kDa, 32A kDa, 32B kDa, 45 kDa, 58 kDa, 71 kDa, 80 kDa, 110 kDa and respective analogs, homologs, subunits and degenerative variants thereof including recombinant non-fusion proteins, fusion proteins and derivatives thereof. (See U.S. Pat. Ser. No. 6,752,993 and 6,599,510, the entire contents of which are hereby incorporated by reference). It is apparent to those of ordinary skill in the art that the molecular weights used to identify the major extracellular proteins of *Mycobacteria* and other intracellular pathogens are only intended to be approximations. Those skilled in the art of recombinant technology and molecular biology will realize that it is possible to co-express (co-translate) these proteins with additional amino acids, polypeptides and proteins, as it is also possible to express these proteins in truncated forms. The resulting modified proteins are still considered to be within the scope of the present invention whether termed native, non-fusion proteins, fusion proteins, hybrid proteins or chimeric proteins. For the purposes of the present invention, fusion proteins are defined to include, but not limited to, the products of two or more coding sequences from different genes that have been cloned together and that, after translation, form a single polypeptide sequence.

Antigen expression, including extracellular proteins, is generally enhanced when genes encoding for recombinant non-fusion proteins are located on, and under the control of, one or more plasmids (extrachromosomal DNA) rather than integrated into the host genome. Moreover, protein expression driven by promoter sequences specific for a particular protein provide enhanced expression and improved protein folding and processing of non-fusion-protein antigens. Therefore, the present invention provides recombinant extracellular non-fusion proteins encoded on extrachromosomal DNA that are controlled by non-heat shock gene promoters or non-stress protein gene promoters, preferably protein-specific promoter sequences.

The present invention provides recombinant attenuated intracellular pathogen immunogenic compositions such as rBCG that express their own endogenous extracellular proteins in addition to recombinant extracellular non-fusion proteins of closely related and/or other intracellular pathogens. However, it has been demonstrated through 80 years of studies that BCG's endogenous extracellular proteins alone do not provide complete protection in all recipients. Furthermore, as will be explained in greater detail below, the present inventors have also demonstrated that merely co-injecting *M. tuberculosis* extracellular proteins along with traditional BCG does not result in immunogenic compositions superior to BCG alone.

In one embodiment of the present invention the immunogenic composition includes a recombinant BCG immunogenic composition expressing only one immunogen, for example, but not limited to, the 23.5 kDa, 30 kDa, or 32 kDa major extracellular proteins of *M. tuberculosis*. In another embodiment of the present invention the recombinant BCG may express two or more immunogens, for example the 23.5 kDa and the 30 kDa major extracellular proteins of *M. tuberculosis*. This latter embodiment may be particularly effective as a immunogenic composition for preventing diseases in mammals. The present inventors have proposed the non-limiting theory that the simultaneous over expression of the 23.5 kDa and the 30 kDa major extracellular proteins of *M. tuberculosis* by a recombinant BCG may act synergistically to heighten the mammalian immune response against the intracellular pathogens of the present invention. This theory is partially based on the observation that wild-type and recombinant BCG are deletion mutants of *M. bovis* that do not naturally express their own 23.5 kDa major extracellular protein.

However, immunogenic compostions utilizing BCG as the transformant can cause disseminated disease in immunocompromised persons such as those with AIDS. In rare cases the disseminated disease can be fatal. Therefore, in another embodiment of the present invention recombinant BCG strains, using BCG Tice as the wild-type parent, that are anticipated to be safe for use in eliciting an immune response in immunocompromised hosts have been developed. Four of these strains are auxotrophs and hence they multiply only in the presence of excess amounts of the amino acid for which they are auxotrophic. In one embodiment of the present invention non-limiting exemplary examples include BCG tryptophan or glutamine auxotrophs. For this reason, their growth is regulatable by the host as will be discussed further below. Two additional BCG strains suitable for use in immunosuppressed, or partially immunosuppresed mammals are not auxotrophs and hence not growth-regulatable. These non-auxotrophic BCG strains are allelic exchange mutants and are anticipated to be attenuated in immunocompromised hosts.

However, as previously stated, the present invention is not limited to auxotrophic strains of the transformant. The present inventors anticipate that auxotrophS may not be suitable for all applications where the present immunogenic compositions are desirable. For example, while auxotrophs are useful in regulating the transformant's growth in vivo, it requires that a second composition be administered timely and consistently to assure that the host develops the desired immune response. This requires vigilance on both the administering personal, the host and the host's care giver. Consequently, when the risk disseminated immunogenic composition-associated disease is minimal, it is more desirable to administer a non-auxotrophic transformant. Therefore, the following description pertaining to making the various embodiments of the present invention, including the genetic constructs, plasmids, and pharmaceutical compositions apply equally to both auxotrophic as well as non-auxotrophic transformants.

Persons having ordinary skill in the art of microbiology will readily understand that the following growth conditions, media, temperature, times etc. are generally the same for auxotrophs and non-auxotrophs except that the essential nutrient will be required for auxotrophic growth. Moreover, persons having ordinary skill in the art of immunology will understand that the administrations of immunogenic compostions to a host are the same for both auxotrophic and non-auxotrophic compostions.

In one exemplary embodiment of the present invention, the recombinant BCG immunogenic compositions express *M. tuberculosis* major extracellular proteins utilizing plasmid pNBV1 and a promoter from the upstream region immediately adjacent to the glutamine synthetase gene (glnA1). In another exemplary embodiment, the recombinant BCG immunogenic compositions express *M. tuberculosis* major extracellular proteins utilizing plasmid pNBV1 and a promoter from the upstream region immediately adjacent to the gene encoding the extracellular protein. In yet another exemplary embodiment of the present invention, the recombinant BCG immunogenic compositions express *M. bovis* 30 kDa major extracellular protein utilizing plasmid pNBV1 and a promoter from the upstream region immediately adjacent to the gene encoding the 30 kDa extracellular protein. In another exemplary embodiment, the recombinant BCG immunogenic compositions express *M. leprae* 30 kDa major extracellular protein utilizing plasmid pNBV1 and a promoter from the upstream region immediately adjacent to the gene encoding the 30 kDa extracellular protein.

For brevity sake, and due to the immensely complex description that would ensue, but not intended as a limitation, the present invention will be more specifically described using a recombinant BCG (rBCG) as the vaccination agent and *M. tuberculosis, M. bovis* and *M. leprae* extracellular non-fusion proteins, specifically the 23.5 kDa, 30 kDa and 32A kDa major extracellular non-fusion proteins of *M. tuberculosis* and the 30 kDa, major extracellular non-fusion proteins of *M. bovis* and *M. leprae* as an exemplary embodiment of the present invention. Furthermore, as example of multiple heterologous antigen over expression and secretion the 23.5 kDa and 30 kDa major extracellular non-fusion proteins of *M. tuberculosis* will be co-expressed and secreted from rBCG.

It is understood that any recombinant immunogenic antigen may be expressed by any recombinant attenuated intracellular pathogen. Furthermore, the immunogenic compositions of the present invention are not limited to rBCG as the immunogenic composition. Moreover, the immunogens are not limited to the major extracellular non-fusion proteins of *M. tuberculosis, M. bovis* and *M. leprae.*

In order to determine the effects of immunogenic composition strain variation, different BCG strains were used to prepare the various embodiments of the present invention: BCG Tice and BCG Connaught. Wild-type *M. bovis* BCG Tice was purchased from Organon and wild-type *M. bovis* BCG Connaught was obtained from Connaught Laboratories, Toronto, Canada. The strains were maintained in 7H9 medium pH 6.7 (Difco) at 37° C. in a 5% $CO_2$-95% air atmosphere as unshaken cultures. Cultures were sonicated once or twice weekly for 5 min in a sonicating water bath to reduce bacterial clumping.

Immunogenic Compostions Suitable for Use in Non-immunocompromised Hosts

A. Recombinant BCG TICE (rBCG30 Tice)

Recombinant BCG TICE (rBCG30 Tice) expressing the *M. tuberculosis* 30 kDa major extracellular non-fusion protein was prepared as follows. The plasmid pMTB30, a recombinant construct of the *E. coli/mycobacteria* shuttle plasmid pSMT3, was prepared as previously described by the present inventors in Harth, G., B. -Y. Lee and M. A. Horwitz. 1997. High-level heterologous expression and secretion in rapidly growing nonpathogenic mycobacteria of four major *Mycobacterium tuberculosis* extracellular proteins considered to be leading immunogenic composition candidates and drug targets. Infect. Immun. 65:2321–2328, the entire contents of which are hereby incorporated by reference.

B. Recombinant BCG30 Tice II (pNBV1-pglnA-MTB30)

Recombinant BCG30 Tice II (pNBV1-pglnA-MTB30), which over expresses the *M. tuberculosis* 30 kDa extracellular non-fusion protein, was prepared as follows. Plasmid pNBV1-pglnA1-MTB30 was constructed by amplifying the coding region of the *M. tuberculosis* 30 kDa gene (including an NdeI restriction site at the start codon and a HindIII restriction site immediately downstream of the stop codon) and cloning this PCR product downstream of the *M. tuberculosis* glnA1 promoter in the NdeI→HindIII sites of pNBV1-BFRB (Tullius, M., G. Harth, and M. A. Horwitz. 2001. The high extracellular levels of *Mycobacterium tuberculosis* glutamine synthetase and superoxide dismutase are primarily due to high expression and extracellular stability rather than to a protein specific export mechanism. Infect. Immun. 69:6348–6363). After confirming by restriction analysis that the plasmid was correct, the plasmid was electroporated into *M. bovis* BCG Tice and transformants were selected on 7H11 agar with 50 $\mu$g $mL^{-1}$ hygromycin. Several individual hygromycin resistant clones were randomly selected and cultured in 7H9 medium containing 50 $\mu$g $mL^{-1}$ hygromycin. The expression and export of recombinant *M. tuberculosis* 30 kDa protein were verified by polyacrylamide gel electrophoresis and immunoblotting with polyvalent, highly specific rabbit anti-30 kDa protein immunoglobulin. rBCG30 Tice II was found to produce 24 times more 30 kDa antigen per mL of culture than BCG Tice harboring just the vector (pNBV1).

C. Recombinant BCG23.5 Tice I (pNBV1-pglnA-MTB23.5)

Recombinant BCG23.5 Tice I (pNBV1-pglnA-MTB23.5), which over expresses the *M. tuberculosis* 23.5 kDa extracellular non-fusion protein, was prepared as follows. Plasmid pNBV1-pglnA1-MTB23.5 was constructed by amplifying the coding region of the *M. tuberculosis* 23.5 kDa gene (including an NdeI restriction site at the start codon and BamHI and HindIII restriction sites immediately downstream of the stop codon) and cloning this PCR product downstream of the *M. tuberculosis* glnA1 promoter in the NdeI→HindIII sites of pNBV1-BFRB (Tullius, M., G. Harth, and M. A. Horwitz. 2001. The high extracellular levels of *Mycobacterium tuberculosis* glutamine synthetase and superoxide dismutase are primarily due to high expression and extracellular stability rather than to a protein specific export mechanism. Infect. Immun. 69:6348–6363). After confirming by restriction analysis that the plasmid was correct, the plasmid was electroporated into *M. bovis* BCG Tice and transformants were selected on 7H11 agar with 50 $\mu$g $mL^{-1}$ hygromycin. Several individual hygromycin resistant clones were randomly selected and cultured in 7H9 medium containing 50 $\mu$g $mL^{-1}$ hygromycin. The expression and export of recombinant *M. tuberculosis* 23.5 kDa protein were verified by polyacrylamide gel electrophoresis and immunoblotting with polyvalent, highly specific rabbit anti-23.5 kDa protein immunoglobulin. rBCG23.5 Tice I produced the 23.5 kDa protein at a high level that was equivalent to or slightly greater than the amount of recombinant 30 kDa protein produced by rBCG30 Tice II. Because BCG does not have a gene encoding the 23.5 kDa protein, no comparison could be made to the parental strain as was done for the 30 kDa protein. (BCG Tice does not express a 23.5 kDa protein because of the RD2 genomic deletion of ~11.5 kb, which encompasses the corresponding *M. tuberculosis* genes Rv1978 to Rv1988 [23.5 kDa protein gene=Rv 1980]; the deletion occurred during the generation of BCG strains from wild-type *M. bovis* before 1931).

D. Recombinant BCG30/23.5 Tice I (pNBV1-pglnA-MTB30/23.5)

Recombinant BCG30/23.5 Tice I (pNBV1-pglnA-MTB30/23.5), which over expresses the *M. tuberculosis* 30 kDa and 23.5 kDa extracellular non-fusion protein, was prepared as follows. Plasmid pNBV1-pglnA1-MTB30/23.5 was constructed by cloning a 1 kb BamHI fragment from pNBV1-pglnA1-MTB23.5 (which includes the *M. tuberculosis* glnA1 promoter and the 23.5 kDa coding region in their entirety) into the unique BamHI site of pNBV1-pglnA1-MTB30. The genes encoding the two proteins are oriented in the same direction on the plasmid with the gene encoding the 23.5 kDa protein upstream of the gene encoding the 30 kDa protein. After confirming by restriction analysis that the plasmid was correct, the plasmid was electroporated into *M. bovis* BCG Tice and transformants were selected on 7H11 agar with 50 $\mu$g $mL^{-1}$ hygromycin. Several individual hygromycin resistant clones were randomly selected and cultured in 7H9 medium containing 50 $\mu$g $mL^{-1}$ hygromycin. The expression and export of recombinant *M. tuberculosis* 30 kDa and 23.5 kDa proteins were verified by polyacrylamide gel electrophoresis and immunoblotting with polyvalent, highly specific rabbit anti-30 kDa protein and anti-23.5 kDa protein immunoglobulin. rBCG30/23.5 Tice I was found to produce 24 times more 30 kDa antigen per mL of culture than BCG Tice harboring just the vector (pNBV1). This strain also produced the 23.5 kDa protein at a high level that was slightly greater than the amount of recombinant 30 kDa protein. Because BCG does not have a gene encoding the 23.5 kDa protein, no comparison could be made with the parental strain as was done for the 30 kDa protein.

E. Recombinant BCG30 Tice III (pNBV-1-MTB30)

Recombinant BCG30 Tice Ill (pNBV-1-MTB30), which over expresses the *M. tuberculosis* 30 kDa major extracellular protein, was prepared as follows. This recombinant strain was generated by electroporating the recombinant plasmid pNBV1, consisting of the vector backbone and a ~1.5 kilo basepairs (kb) piece of *M. tuberculosis* Erdman DNA flanked by ClaI and BamHI restriction sites and containing the coding region of the 30 kDa major extracellular protein and the promoter region immediately upstream of the coding region, into BCG Tice bacteria (Stock #2). The strain stably maintained the recombinant plasmid, and the level of recombinant 30 kDa protein expression remained almost constant over a 12 month period in the absence of antibiotics, as confirmed by immunoblotting with 30 kDa protein specific antisera (14.4-fold over the BCG Tice wild-type background level at the beginning of the analysis and 11.5-fold at the end of the analysis). A stock (Stock #1) was established in 10% glycerol at a concentration of $2.5\times10^8$ Particles/ml and stored at −80° C.

F. Recombinant BCG23.5 Tice II (pNBV-1-MTB23.5)

Recombinant BCG23.5 Tice II (pNBV-1-MTB23.5), which over expresses the *M. tuberculosis* 30 kDa major extracellular protein, was prepared as follows. This recombinant strain was generated by electroporating the recombinant plasmid pNBV1, consisting of the vector backbone and a ~1.4 kilo basepairs (kb) piece of *M. tuberculosis* Erdman DNA flanked by PstI and BamHI restriction sites and containing the coding region of the 23.5 kDa major extracellular protein and the promoter region immediately upstream of the coding region, into BCG Tice bacteria (Stock #2). The strain stably maintained the recombinant plasmid, and the level of recombinant 23.5 kDa protein expression remained almost constant over a 12 month period in the absence of antibiotics, as confirmed by immunoblotting with 23.5 kDa protein specific antisera (16.2 mg/L at the beginning of the analysis and 15.1 mg/L at the end of the analysis. Because BCG does not have a gene encoding the 23.5 kDa protein, no comparison could be made with the parental strain as was done for the 30 kDa protein. A stock (Stock #1) was established on Aug. 24, 2001 in 10% glycerol at a concentration of $3\times10^8$ Particles/ml and stored at −80° C.

G. Recombinant BCG30/23.5 Tice IIA (pNBV1-MTB30/23.5↑↑)

Recombinant BCG30/23.5 Tice IIA (pNBV1-MTB30/23.5↑↑) (as used herein after "↑↑" refers to a genetic construct encoding for multiple major extracellular proteins where in the nucleic acid sequences encoding for each protein [genes] are orientated in the same direction relative to 5' end of the genetic construct) over expresses both the *M. tuberculosis* 30 kDa and 23.5 kDa major extracellular proteins. The genes encoding the two proteins are oriented in the same direction. This recombinant strain was generated by electroporating the recombinant plasmid pNBV1, consisting of the vector backbone and two pieces of *M. tuberculosis* Erdman DNA of ~1.5 and ~1.4 kb, flanked by ClaI and NdeI (30 kDa protein gene and promoter) and NdeI and NdeI-BamHI (23.5 kDa protein gene and promoter) restriction sites and containing the coding and promoter regions immediately upstream of each of the two coding regions of the 30 and 23.5 kDa major extracellular proteins, into BCG Tice bacteria (Stock #2). The strain stably maintained the recombinant plasmid, and the level of recombinant 30 and 23.5 kDa protein expression remained almost constant over a 12 month period in the absence of antibiotics, as confirmed by immunoblotting with 30 and 23.5 kDa protein specific antisera (For the 30 kDa protein, expression was 23.3-fold over the BCG Tice wild-type background level at the beginning of the analysis and 16.5-fold over the BCG Tice wild-type background level at the end of the analysis; for the 23.5 kDa protein, expression was 18.7 mg/L at the beginning of the analysis and 12.2 mg/L at the end of the analysis). As mentioned above, expression of the recombinant 23.5 kDa protein is measured in absolute terms because BCG Tice does not express a 23.5 kDa protein. A stock (Stock #1) was established in 10% glycerol at a concentration of $3\times10^8$ Particles/ml and stored at −80° C.

H. Recombinant BCG30/23.5 Tice IIB (pNBV1-MTB30/23.5↑↓)

Recombinant BCG30/23.5 Tice IIB (pNBV1-MTB30/23.5↑↓) (as used herein after "↑↓" refers to a genetic construct encoding for multiple major extracellular proteins where in the nucleic acid sequences encoding for each protein [genes] are orientated in the opposite direction relative to 5' end of the genetic construct) over expresses both the *M. tuberculosis* 30 kDa and 23.5 kDa major extracellular proteins. The genes encoding the two proteins are oriented in opposite directions on the plasmid. This recombinant strain was generated by electroporating the recombinant plasmid pNBV1, consisting of the vector backbone and two pieces of *M. tuberculosis* Erdman DNA of ~1.5 and ~1.4 kb, flanked by ClaI and NdeI (30 kDa protein gene and promoter) and NdeI and NdeI-BamHI (23.5 kDa protein gene and promoter) restriction sites and containing the coding and promoter regions immediately upstream of the coding regions of the 30 and 23.5 kDa major extracellular proteins, into BCG Tice bacteria (Stock #2). In contrast to the strain described just above (rBCG30/23.5 Tice IIA), the orientation of the NdeI restriction fragment carrying the coding and promoter region of the 23.5 kDa protein was inverted. The strain stably maintained the recombinant plasmid, and the level of recombinant 30 and 23.5 kDa protein expression remained almost constant over a 12 month period in the absence of antibiotics, as confirmed by immunoblotting with 30 and 23.5 kDa protein specific antisera. (For the 30 kDa protein, expression was 25.7-fold over the BCG Tice wild-type background level at the beginning of the analysis and 21.1-fold over the BCG Tice wild-type background level at the end of the analysis; for the 23.5 kDa protein, expression was 16.6 mg/L at the beginning of the analysis and 12.8 mg/L at the end of the analysis). As mentioned above, expression of the recombinant 23.5 kDa protein is measured in absolute terms because BCG Tice does not express a 23.5 kDa protein. A stock (Stock #1) was established in 10% glycerol at a concentration of $3\times10^8$ Particles/ml and stored at −80° C.

I. Recombinant BCG32A Tice I (pNBV1-MTB32A)

Recombinant BCG32A Tice I (pNBV1-MTB32A), which over expresses the *M. tuberculosis* 32A kDa major extracellular protein (a.k.a. Antigen 85A), was prepared as follows. This recombinant strain was generated by electroporating the recombinant plasmid pNBV1, consisting of the vector backbone and a ~1.5 kb piece of *M. tuberculosis* Erdman DNA flanked by ClaI and BamHI restriction sites and containing the coding region of the 32A kDa major extracellular protein and the promoter region immediately upstream of the coding region, into BCG Tice bacteria (Stock #2). The strain stably maintained the recombinant plasmid, and the level of recombinant 32A kDa protein expression remained almost constant over a 12 month period in the absence of antibiotics, as confirmed by immunoblotting with 32A kDa protein specific antisera (10.5-fold over the BCG Tice wild-type background level at the beginning of the analysis and 8.1-fold at the end of the analysis). A stock (Stock #1) was established in 10% glycerol at a concentration of $3\times10^8$ Particles/ml and stored at −80° C.

J. Recombinant BCG(MB)30 Tice (pNBV1-MB30)

Recombinant BCG(MB)30 Tice (pNBV1-MB30),which over expresses the *M. bovis* 30 kDa major extracellular protein, was prepared as follows. This recombinant strain was generated by electroporating the recombinant plasmid pNBV1, consisting of the vector backbone and a ~1.5 kb piece of *M. bovis* wild-type (ATCC#19210) DNA flanked by ClaI and BamHI restriction sites and containing the coding region of the 30 kDa major extracellular protein and the promoter region immediately upstream of the coding region, into BCG Tice bacteria (Stock #2). The strain stably maintained the recombinant plasmid, and the level of recombinant 30 kDa protein expression remained almost constant over a 12 month period in the absence of antibiotics, as confirmed by immunoblotting with 30 kDa protein specific antisera (9.7-fold over the BCG Tice wild-type background level at the beginning of the analysis and 7.8-fold at the end of the analysis). A stock (Stock #2) was established in 10% glycerol at a concentration of $2.5\times10^8$ Particles/ml and stored at −80° C.

K. Recombinant BCG(ML)30 Tice (pNBV1-ML30)

Recombinant BCG(ML)30 Tice (pNBV1-ML30), which expresses the *M. leprae* 30 kDa major extracellular protein, was prepared as follows. This recombinant strain was generated by electroporating the recombinant plasmid pNBV1, consisting of the vector backbone and a ~1.3 kb piece of *M. leprae* DNA flanked by ClaI and BamHI restriction sites and containing the coding region of the 30 kDa major extracellular protein and the promoter region immediately upstream of the coding region, into BCG Tice bacteria (Stock #2). The strain stably maintained the recombinant plasmid, and the level of recombinant 30 kDa protein expression remained almost constant over a 12 month period in the absence of antibiotics, as confirmed by immunoblotting with 30 kDa protein specific antisera (9.7-fold over the BCG Tice wild-type background level at the beginning of the analysis and 9.3-fold at the end of the analysis). A stock (Stock #1) was established in 10% glycerol at a concentration of $3\times10^8$ Particles/ml and stored at −80° C.

Immunogenic Compostions Suitable for Use in Immunocompromised Hosts

I. Development of Growth-Regulatable BCG (Auxotrophs)

A. BCG Tice glnA1

The BCG Tice glnA1 gene was disrupted via allelic exchange using the plasmid pEX1-Mtb-glnA1::$Km^r$ which we previously used to generate an *M. tuberculosis* glnA1 mutant (, M. V., G. Harth, and M. A. Horwitz. 2003. Glutamine Synthetase (GlnA1) is essential for growth of *Mycobacterium tuberculosis* in human macrophages and in guinea pigs. Infect. Immun. Vol. 71:7). pEX1-Mtb-glnA1::$Km^r$ was derived from the temperature sensitive-sacB vector, pPR27, and contains a $hyg^r$ gene and a 1.8 kb fragment containing the *M. tuberculosis* glnA1 locus with a $Km^r$ cassette inserted into a unique site located near the middle of the glnA1 coding region. (Pelicic, V., M. Jackson, J. M. Reyrat, W. R. Jacobs, Jr., B. Gicquel, and C. Guilhot. 1997. Efficient allelic exchange and transposon mutagenesis in *Mycobacterium tuberculosis*. Proc. Natl. Acad. Sci. USA 94:10955–10960.) pEX1-Mtb-glnA1::$Km^r$ was electroporated into BCG Tice and transformants were selected on 7H11 containing 50 $\mu$g $mL^{-1}$ hygromycin. The plates were initially kept at the permissive temperature (32° C.) for 6 days and then incubated at the restrictive temperature (39° C.) for 46 days. A single transformant was grown in 7H9-10% OADC-0.05% TWEEN-80 broth culture with 50 $\mu$g $mL^{-1}$ kanamycin and 20 mM L-glutamine at the restrictive temperature for approximately 25 generations and then plated on 7H11 containing 2% (w/v) sucrose, 20 mM L-glutamine, and 50 $\mu$g $mL^{-1}$ kanamycin to select for clones that had undergone a second homologous recombination event. Twelve of 35 randomly selected $Km^r$ clones were found to have the correct phenotype (i.e. $Hyg^s$ and glutamine auxotroph). To ensure a pure culture, we plated one of the twelve clones at low density and a single colony was reisolated. Initial freezer stocks of the strain were prepared from the reisolated clone. Correct genotype of the mutant was confirmed by Southern blot analysis.

The BCG Tice glnA1 strain is a glutamine auxotroph. No growth was observed on 7H11 plates without the addition of L-glutamine. Furthermore, the glnA1 mutant displayed little or no intracellular growth in human macrophages when macrophages were cultured in tissue culture medium containing 0.2 mM L-glutamine (conditions under which the wild-type strain grows normally). However, intracellular growth similar to the wild-type strain was achieved by adding a large excess of L-glutamine (10 mM) to the tissue culture medium. Complementation analysis was performed by transforming BCG Tice glnA1 with plasmids containing the *M. tuberculosis* glnA1 gene (pNBV1-MtbGS) or the *S. typhimurium* ginA gene (pNBV1-StGS). Both plasmids restored a wild-type growth phenotype to the mutant.

The L-glutamine requirement of this BCG glnA1 auxotroph is expected to be very similar to that of an *M. tuberculosis* glnA1 strain that the present inventors have previously characterized in greater detail (Tullius, M. V., G. Harth, and M. A. Horwitz. 2003. Glutamine Synthetase (GlnA1) is essential for growth of *Mycobacterium tuberculosis* in human macrophages and in guinea pigs. Infect. Immun. Vol. 71:7). In the case of the *M. tuberculosis* glnA1 strain, high levels of L-glutamine (10–20 mM) were required in solid medium for the mutant to grow normally. In liquid medium, the *M. tuberculosis* glnA1 mutant grew at a normal growth rate at >1 mM L-glutamine. Although initially growth was normal at 1–2 mM L-glutamine, these cultures did not reach as high a density as cultures containing 5 mM and 20 mM L-glutamine, and they exhibited a sharp drop in viability shortly after log-phase. The *M. tuberculosis* glnA1 strain lost viability rapidly when diluted into medium lacking L-glutamine. No growth of the *M. tuberculosis* glnA1 mutant occurred in human macrophages when the macrophages were cultured in the presence of 0.2 mM L-glutamine, a condition under which the wild-type strain grows normally. Growth of the *M. tuberculosis* glnA1 mutant in human macrophages was poor when macrophages were cultured in standard tissue culture medium containing 2 mM L-glutamine. However, intracellular growth similar to the wild-type strain was achieved when macrophages were cultured in a large excess of L-glutamine (10 mM). The *M. tuberculosis* glnA1 mutant is highly attenuated in the guinea pig model of pulmonary tuberculosis.

B. BCG Tice trpD

The BCG Tice trpD gene was disrupted via allelic exchange. The allelic exchange substrate was generated using a PCR strategy in which a BCG Tice trpD locus with a 588 bp deletion was created and a $Km^r$ cassette was inserted at the site of the deletion. This mutated allele was cloned into the allelic exchange vector pEX2 (a derivative of pEX1 in which the gfpuv gene, encoding green fluorescent protein, is replaced by the *E. coli* codBA operon, encoding cytosine deaminase) to generate pEX2 ΔtrpD::$Km^r$ (Tullius, M. V., G. Harth, and M. A. Horwitz. 2003. Glutamine Synthetase (GlnA1) is essential for growth of *Mycobacterium tuberculosis* in human macrophages and in guinea pigs. Infect. Immun. Vol. 71:7).

pEX2 ΔtrpD::$Km^r$ was electroporated into BCG Tice and transformants were selected on 7H11 containing 50 $\mu$g $mL^{-1}$ hygromycin at the permissive temperature (32° C.). Pooled transformants were grown in 7H9-10% OADC-0.05% TWEEN-80 broth culture with 10 $\mu$g $mL^{-1}$ kanamycin and 50 $\mu$g $mL^{-1}$ L-tryptophan at the permissive temperature for approximately 10 generations and then plated on 7H10 containing 2% (w/v) sucrose, 50 $\mu$g $mL^{-1}$ kanamycin, and 50 $\mu$g $mL^{-1}$ L-tryptophan at the restrictive temperature (39° C.) to select for clones that had undergone a homologous recombination event. Four of 10 selected $Km^r$ clones were found to have the correct phenotype (i.e. $Hyg^s$ and tryptophan auxotroph). To ensure a pure culture, one of the four clones was plated at low density and a single colony was reisolated. Initial freezer stocks of the strain were prepared from the reisolated clone. Correct genotype of the mutant was confirmed by Southern blot analysis.

The BCG Tice trpD strain is a tryptophan auxotroph. No growth was observed on 7H11 plates without the addition of L-tryptophan. In broth culture, the BCG Tice trpD strain grew at a rate similar to the wild-type strain in the presence of >10 $\mu$g $mL^{-1}$ L-tryptophan. Growth was nearly twice as slow at 3 $\mu$g $mL^{-1}$ L-tryptophan and the strain lost viability when diluted into medium lacking L-tryptophan. The trpD mutant displayed little or no intracellular growth in human macrophages when macrophages were cultured in standard tissue culture medium which contains 5 $\mu$g $mL^{-1}$ (conditions under which the wild-type strain grows normally). However, intracellular growth similar to the wild-type strain was achieved by adding an additional 100 $\mu$g $mL^{-1}$ L-tryptophan to the tissue culture medium. Complementation analysis was performed by transforming BCG Tice trpD with a plasmid containing the BCG Tice trpD gene (pNBV1-trpD). This plasmid restored a wild-type growth phenotype to the mutant.

II. Growth-regulatable BCG Overexpressing the *M. tuberculosis* 30 kDa Major Secretory Protein (Auxotrophs)

A. BCG Tice glnA1 pSMT3-MTB30

The plasmid pSMT3-MTB30 was electroporated into BCG Tice glnA1 and transformants were selected on 7H11 agar with 50 $\mu$g $mL^{-1}$ hygromycin, 50 $\mu$g $mL^{-1}$ kanamycin, and 20 mM L-glutamine. Two individual hygromycin and kanamycin resistant clones were randomly selected and cultured in 7H9 medium containing 50 $\mu$g $mL^{-1}$ hygromycin, 50 $\mu$g $mL^{-1}$ kanamycin, and 20 mM L-glutamine. The expression and export of recombinant *M. tuberculosis* 30 kDa protein were verified by polyacrylamide gel electrophoresis and immunoblotting with polyvalent, highly specific rabbit anti-30 kDa protein immunoglobulin. BCG Tice glnA1 pSMT3-MTB30 was found to produce ~10–20 times more 30 kDa antigen per mL of culture than BCG Tice glnA1. BCG Tice glnA1 pSMT3-MTB30, like its parent strain BCG Tice glnA1, is a glutamine auxotroph.

B. BCG Tice trpD pSMT3-MTB30

The plasmid pSMT3-MTB30 was electroporated into BCG Tice trpD and transformants were selected on 7H11 agar with 50 $\mu$g $mL^{-1}$ hygromycin, 50 $\mu$g $mL^{1}$ kanamycin, and 50 $\mu$g $mL^{-1}$ L-tryptophan. Ten individual hygromycin and kanamycin resistant clones were randomly selected and cultured in 7H9-10% OADC-0.05% TWEEN-80 broth containing 50 $\mu$g $mL^{-1}$ hygromycin, 50 $\mu$g $mL^{-1}$ kanamycin, and 50 $\mu$g $mL^{-1}$ L-tryptophan. The expression of recombinant *M. tuberculosis* 30 kDa protein was verified by polyacrylamide gel electrophoresis and immunoblotting with polyvalent, highly specific rabbit anti-30 kDa protein immunoglobulin. BCG Tice trpD pSMT3-MTB30 was found to produce ~10–20 times more 30 kDa antigen per mL of culture than a control BCG Tice strain.

III. Attenuated BCG (Non-Auxotroph) BCG Tice narG

The BCG Tice narG gene (encoding nitrate reductase alpha subunit) was disrupted via allelic exchange. The allelic exchange substrate was generated using a PCR strategy in which a BCG Tice narG locus with a 2952 bp deletion was created and a $Km^r$ cassette was inserted at the site of the deletion. This mutated allele was cloned into the allelic exchange vector pEX2 (a derivative of pEX1 in which the gfpuv gene is replaced by the *E. coli* codBA operon) to generate pEX2 ΔnarG::$Km^r$-(Tullius, M. V., G. Harth, and M. A. Horwitz. 2003. Glutamine Synthetase (GlnA1) is essential for growth of *Mycobacterium tuberculosis* in human macrophages and in guinea pigs. Infect. Immun. Vol. 71:7).

pEX2 ΔnarG::$Km^r$ was electroporated into BCG Tice (12–13–2001) and transformants were selected on 7H11 agar containing 50 $\mu$g $mL^{-1}$ hygromycin and 50 $\mu$g $mL^{-1}$ kanamycin at the permissive temperature (32° C.). Pooled transformants were grown in 7H9-10% OADC-0.05%

TWEEN-80 broth culture with 10 $\mu$g mL$^{-1}$ kanamycin at the permissive temperature for approximately 30 generations and then plated on 7H10 agar containing 2% (w/v) sucrose and 10 $\mu$g mL$^{-1}$ kanamycin at the restrictive temperature (39° C.) to select for clones that had undergone a homologous recombination event. Eight of 8 selected Km$^r$ clones were found to have the correct phenotype (i.e. Hyg$^s$). To ensure a pure culture, one of the eight clones was plated at low density and a single colony was reisolated. Initial freezer stocks of the strain were prepared from the reisolated clone. Correct genotype of the mutant was confirmed by Southern blot analysis, demonstrating that the mutant lacked a full length narG.

The narG mutant grows normally on plates, in broth culture, and intracellularly in macrophages. However, a BCG narG mutant generated elsewhere has been reported to be highly attenuated, compared with the parent BCG strain, in an immunodeficient SCID mouse model (Weber, I., Fritz, C., Ruttkowski. S., Kreft, A., and F. C. Bang. 2000. Anaerobic nitrate reductase (narGHJI) activity of *Mycobacterium bovis* BCG in vitro and its contribution to virulence in immunodeficient mice. Mol. Microbiol. 35(5):1017–1025). Hence, it is anticipated that narG mutant strain will similarly be attenuated in SCID mice and, in addition, be attenuated in immunocompromised persons.

IV. Attenuated BCG Overexpressing the *M. tuberculosis* 30 kDa Major Secretory Protein (Non-auxotroph)

BCG Tice narG pSMT3-MTB30

The plasmid pSMT3-MTB30 was electroporated into BCG Tice narG and transformants were selected on 7H11 agar with 50 $\mu$g mL$^{-1}$ hygromycin and 10 $\mu$g mL$^{-1}$ kanamycin. Five individual hygromycin and kanamycin resistant clones were randomly selected and cultured in 7H9-10% OADC-0.05% TWEEN-80 broth containing 50 $\mu$g mL$^{-1}$ hygromycin. The expression of recombinant *M. tuberculosis* 30 kDa protein was verified by polyacrylamide gel electrophoresis and immunoblotting with polyvalent, highly specific rabbit anti-30 kDa protein immunoglobulin. BCG Tice narG pSMT3-MTB30 was found to produce ~10–20 times more 30 kDa antigen per mL of culture than a control BCG Tice strain.

It is understood that using the methods described above in conjunction with methods known to those skilled in the art of recombinant DNA technology, recombinant BCG strains (both auxotrophs and non-auxotrophs) expressing the *M. tuberculosis* 32(A) kDa major extracellular non-fusion protein, 16 kDa major extracellular non-fusion protein, 23.5 kDa major extracellular non-fusion protein, and other *M. tuberculosis* major extracellular non-fusion proteins can be prepared. Furthermore, similar methodologies can be used to prepare recombinant BCG strains expressing *M. leprae* major extracellular non-fusion proteins including, but not limited to the *M. leprae* 30 kDa major extracellular non-fusion protein homolog of the *M. tuberculosis* 30 kDa major extracellular non-fusion protein (a.k.a. Antigen 85B), the *M. leprae* 32(A) kDa major extracellular non-fusion protein homolog of the *M. tuberculosis* 32(A) kDa major extracellular non-fusion protein (a.k.a. Antigen 85A), and other *M. leprae* major extracellular non-fusion proteins. Additionally, similar methodologies also can be used to prepare recombinant *M. bovis* BCG expressing the *M. bovis* 30 kDa major extracellular non-fusion protein homolog of the *M. tuberculosis* 30 kDa major extracellular non-fusion protein (a.k.a. Antigen 85B), the *M. bovis* 32(A) kDa major extracellular non-fusion protein homolog of the *M. tuberculosis* 32(A) kDa major extracellular protein (a.k.a. Antigen 85A), and other *M. bovis major extracellular proteins.*

Representative Methods for Plasmid and Transformant Preparation

Briefly, plasmid pMTB30 was engineered to express the *M. tuberculosis* Erdman 30 kDa major extracellular non-fusion protein from its own promoter (or any non-heat shock and non-stress protein gene promoter) by inserting a large genomic DNA restriction fragment containing the 30 kDa non-fusion protein gene plus extensive flanking DNA sequences into the plasmid's multi-cloning site using methods known to those skilled in the art of recombinant DNA technology. The plasmid was first introduced into *E. coli* DH5α to obtain large quantities of the recombinant plasmid. The recombinant *E. coli* strain, which was unable to express the *M. tuberculosis* 30 kDa non-fusion protein, was grown in the presence of 250 $\mu$g/ml hygromycin and the plasmid insert's DNA sequence was determined in its entirety. The plasmid was introduced into *M. smegmatis* by electroporation using 6.25 kV/cm, 25 $\mu$F, and 1000 mΩ as the conditions yielding the largest number of positive transformants. The present inventors verified the presence of the recombinant plasmid by growth in the presence of 50 $\mu$g/ml hygromycin and the constitutive expression and export of recombinant 30 kDa non-fusion protein by polyacrylamide gel electrophoresis and immuoblotting with polyvalent, highly specific rabbit anti-30 kDa non-fusion protein immunoglobulin using methods known to those skilled in the art of recombinant DNA technology. Additionally, the inventors verified the correct expression and processing of the recombinant *M. tuberculosis* 30 kDa non-fusion protein, which was indistinguishable from its native counterpart by N-terminal amino acid sequencing.

The recombinant pSMT3 plasmid pMTB30 was subsequently introduced into *M. bovis* BCG Tice using 6.25 kV/cm, 25 $\mu$F, and 200 mΩ as the optimal electroporation conditions. Transformants were incubated in 7H9 medium supplemented with 2% glucose for 4 h at 37° C. in an environmental shaker and subsequently plated on 7H11 agar with 20 $\mu$g/ml hygromycin. The concentration of hygromycin was gradually increased to 50 $\mu$g/ml as the transformants were subcultured to a new growth medium. Recombinant BCG Tice cultures were maintained under the same conditions as the wild-type except that the 7H9 medium contained 50 $\mu$g/ml hygromycin.

The expression and export of recombinant *M. tuberculosis* 30 kDa non-fusion protein were verified by polyacrylamide gel electrophoresis and immunoblotting with polyvalent, highly specific rabbit anti-30 kDa non-fusion protein immunoglobulin. Typically, 1 in 10 transformants expressed and exported significantly larger quantities of recombinant non-fusion protein than the other transformants; 2 such transformants were chosen and a large stock of these transformants was prepared and frozen at −70° C. in 7H9 medium containing 10% glycerol. These transformants were used for immunogenic composition efficacy studies in guinea pigs. FIG. 1*a* shows the expression of the *M. tuberculosis* 30 kDa major extracellular non-fusion protein by recombinant BCG Tice on SDS-PAGE gels and immunoblots. The recombinant strain expressed much more of the *M. tuberculosis* 30 kDa major extracellular non-fusion protein than the wild-type both on Coomassie blue stained gels and immunoblots.

Figure 1B:
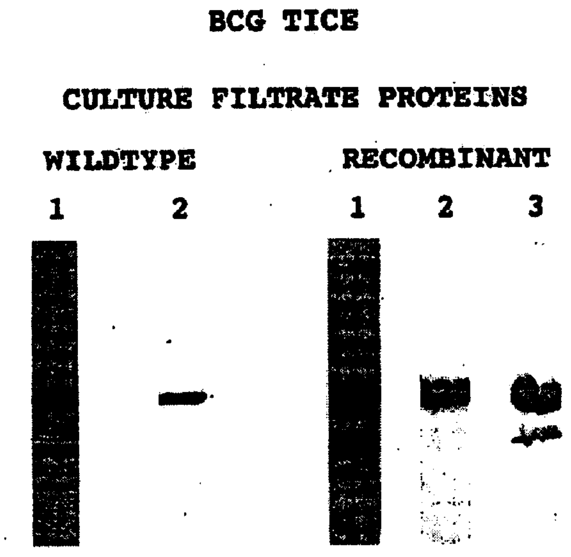

Next a recombinant *M. bovis* BCG Connaught strain (rBCG30 Conn) expressing the *M. tuberculosis* 30 kDa major extracellular non-fusion protein was prepared similarly to that described above for recombinant BCG Tice (rBCG30 Tice) using the aforementioned pMTB30 plasmid. It was maintained in medium containing hygromycin at a concentration of 50 μg/ml under the same conditions as described for the recombinant BCG Tice strain. FIG. 1*b* shows the expression of the *M. tuberculosis* 30 kDa major extracellular non-fusion protein by recombinant BCG Connaught on SDS-PAGE gels and immunoblots. The recombinant strain expressed much more of the *M. tuberculosis* 30 kDa major extracellular non-fusion protein than the wild-type both on Coomassie blue stained gels and immunoblots.

Additionally, the relative expression of major extracellular proteins in rBCG strains utilizing plasmid pNBV1 and a promoter from the upstream region immediately adjacent to the Glutamine Synthetase Gene glnA1 or the gene encoding the extracellular protein was compared to the parental BCG strain. Immunoblots of each of the recombinant protein from each of the recombinant strains were digitized using a CreoScitex EverSmart Jazz scanner and protein bands were densitometrically analyzed by area measurement using the NIH image 1.62 software program. The expression levels of these recombinant proteins are given in Table 8.

Plasmid stability of recombinant strains of BCG was assessed biochemically. This biochemical analysis demonstrated that in the presence of hygromycin, broth cultures of the recombinant BCG strains maintain a steady level of recombinant non-fusion protein expression over a 3 month growth period. In the absence of hygromycin, the same cultures show only a slight decrease of non-fusion protein expression (on a per cell basis), indicating that the recombinant plasmid is stably maintained and only very gradually lost in bacteria growing without selective pressure (FIG. 1*a* and FIG. 1*b*, lane 3).

The stability of the various recombinant BCG strains of the present invention expressing *M. tuberculosis* major extracellular proteins utilizing plasmid pNBV1 and a promoter from the upstream region immediately adjacent to the Glutamine Synthetase Gene glnA1 was examined. Expression of the 30 kDa and/or 23.5 kDa proteins by rBCG30 Tice II, rBCG23.5 Tice I, and rBCG30/23.5 Tice I was stable for at least 3 months of continuous culture (approx. 30 generations) in medium that contained hygromycin for the positive selection of the plasmids. In addition, culture of the strains for one month (approx. 10 generations) in medium lacking hygromycin resulted in no decrease in expression levels. However, after 6 months of continuous culture in the absence of hygromycin (approx. 60 generations) expression of the 30 kDa protein by rBCG30 Tice II was greatly reduced and the expression of the 30 kDa and 23.5 kDa proteins by rBCG30/23.5 Tice I was reduced to undetectable levels. Only expression of the 23.5 kDa protein by rBCG23.5 Tice I remained high. It was confirmed that the drop in expression for the two strains was due to loss of the plasmid from a large percentage of cells in the culture (measured by plating the strains on 7H11 plates with and without hygromycin). rBCG23.5 Tice I exhibited no loss of the plasmid (approx. 100% of cells were hygromycin resistant) consistent with the high expression still maintained after 6 months of culture in the absence of hygromycin.

Additionally, the stability of new recombinant BCG strains expressing *M. tuberculosis, M. bovis,* and *M. leprae* major extracellular proteins utilizing plasmid pNBV1 and a promoter from the upstream region immediately adjacent to the gene encoding the extracellular protein was also examined. Expression of the recombinant proteins, i. e. the 30, 23.5, and 32A kDa major extracellular proteins of *M. tuberculosis* and the 30 kDa major extracellular protein of *M. bovis* and *M. leprae,* was stable for at least 12 months of continuous culture (~120 generations) in medium containing or lacking hygromycin, the positive selection marker for the plasmid pNBV1. No loss of plasmid was detected.

These experiments show that the various recombinant strains exhibited a wide spectrum of stability regarding the levels of expression of recombinant proteins. In general, plasmids containing the coding DNA sequences for the recombinant proteins fused to their endogenous promoter regions quite stably expressed the recombinant proteins for at least 12 months, although the levels typically dropped slightly over time, most likely to balance expression and secretion of recombinant proteins with the metabolic state of the bacterial cell and the expression of the corresponding endogenous proteins. In contrast, strains that contained plasmids where the heterologous glnA1 promoter drove expression of recombinant proteins exhibited great variability in stability of expression over time. It should be noted that the recombinant proteins were identical to those expressed from the above mentioned strains. Variability in expression, therefore, is apparently a function of the promoter sequence.

Representative Methods for Testing Safety and Efficacy of the Immunogenic Compositions of the Present Invention Following the successful immunogenic composition production the immunogenic compositions of the present invention are tested for safety and efficacy using an animal model. The studies utilized guinea pigs because the guinea pig model is especially relevant to human tuberculosis clinically, immunologically, and pathologically. In contrast to the mouse and rat, but like the human, the guinea pig a) is susceptible to low doses of aerosolized *M. tuberculosis;* b) exhibits strong cutaneous DTH to tuberculin; and c) displays Langerhans giant cells and caseation in pulmonary lesions. However, whereas only about 10% of immunocompetent humans who are infected with *M. tuberculosis* develop active disease over their lifetime (half early after exposure and half after a period of latency), infected guinea pigs always develop early active disease. While guinea pigs differ from humans in this respect, the consistency with which they develop active disease after infection with *M. tuberculosis* is an advantage in trials of immunogenic composition efficacy.

The immunization inoculums made in accordance with the teachings of the present invention were prepared from aliquots removed from logarithmically growing wild type or recombinant BCG cultures (the "bacteria"). Each aliquot of bacteria was pelleted by centrifugation at 3,500×g for 15 min and then washed with 1×phosphate buffered saline (1×PBS, 50 mM sodium phosphate pH 7, 150 mM sodium chloride). The immunization inoculums were then resuspended to a final concentration of $1\times10^4$ colony forming units per ml in 1×PBS and contained 1,000 viable bacteria per 100 μl.

Specific-pathogen free 250–300 g outbred male Hartley strain guinea pigs from Charles River Breeding Laboratories, in groups of 9, were immunized intradermally with one of the following: 1) BCG Connaught [$10^3$ Colony Forming Units (CFU)] one time only (time 0 weeks); 2) rBCG30 Connaught ($10^3$ CFU) one time only (time 0 weeks); 3) purified recombinant *M. tuberculosis* 30 kDa major extracellular non-fusion protein (r30), 100 μg in 100 μl Syntex adjuvant formulation (SAF), three times three weeks apart (time 0, 3, and 6 weeks); SAF consisted of Pluronic L121, squalane, and Tween 80, and in the first immunization, alanyl muramyl dipeptide; and 4) SAF only (100 μl) (Sham-immunized), three times three weeks apart (time 0, 3, and 6 weeks). An additional group of 3 animals was sham-immunized with SAF only (100 μl) and used as a skin test control. These and three to six other sham-immunized animals served as uninfected controls in the challenge experiments.

Nine weeks after the only immunization (BCG and rBCG30 groups) or first immunization (r30 group and sham-immunized skin-test group), guinea pigs were shaved over the back and injected intradermally with 10 μg of purified recombinant *M. tuberculosis* 30 kDa major extracellular non-fusion protein (r30) in 100 μl phosphate buffered saline. After 24 hours, the diameter of erythema and induration was measured. (A separate group of sham-immunized animals from the ones used in the challenge studies was used for skin-testing. Sham-immunized animals used in challenge studies were not skin-tested to eliminate the possibility that the skin-test itself might influence the outcome).

Nine weeks after the first or only immunization and immediately after skin-testing, animals were challenged with an aerosol generated from a 10 ml single-cell suspension containing $1\times10^5$ colony-forming units (CFU) of *M. tuberculosis. Mycobacterium tuberculosis* Erdman strain (ATCC 35801) was passaged through outbred guinea pigs to maintain virulence, cultured on 7H11 agar, subjected to gentle sonication to obtain a single cell suspension, and frozen at −70° C. for use in animal challenge experiments. The challenge aerosol dose delivered ~40 live bacilli to the lungs of each animal. The airborne route of infection was used because this is the natural route of infection for pulmonary tuberculosis. A large dose was used so as to induce measurable clinical illness in 100% of control animals within a relatively short time frame (10 weeks). Afterwards, guinea pigs were individually housed in stainless steel cages contained within a laminar flow biohazard safety enclosure and allowed free access to standard laboratory chow and water. The animals were observed for illness and weighed weekly for 10 weeks and then euthanized. The right lung and spleen of each animal were removed and cultured for CFU of *M. tuberculosis.*

Figure 2A:
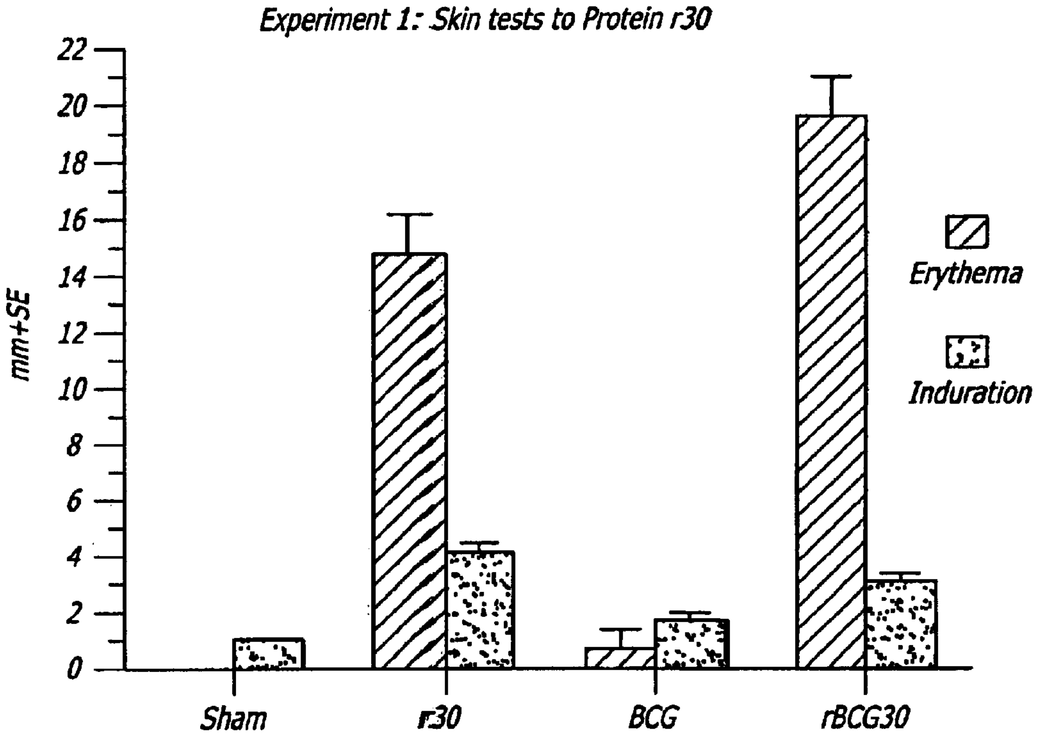
FIG. 2 graphically depicts the results from two experiments labeled 2*a* and 2*b* designed to compare skin tests results of guinea pigs inoculated with the recombinant BCG immunogenic composition expressing the 30 kDa major extracellular protein of *M. tuberculosis*, with BCG alone, with the recombinant 30 kDa protein alone, or with a sham immunogenic composition.
Figure 2B:

In each of the two experiments, the sham-immunized animals and animals immunized with wild-type BCG exhibited little or no erythema and induration upon testing with recombinant 30 kDa *M. tuberculosis* major extracellular non-fusion protein (r30). In contrast, animals immunized with r30 or rBCG30 exhibited marked erythema and induration that was significantly higher than in the sham-immunized or wild-type BCG immunized animals (Table 1 and FIG. 2).

Figure 3A:
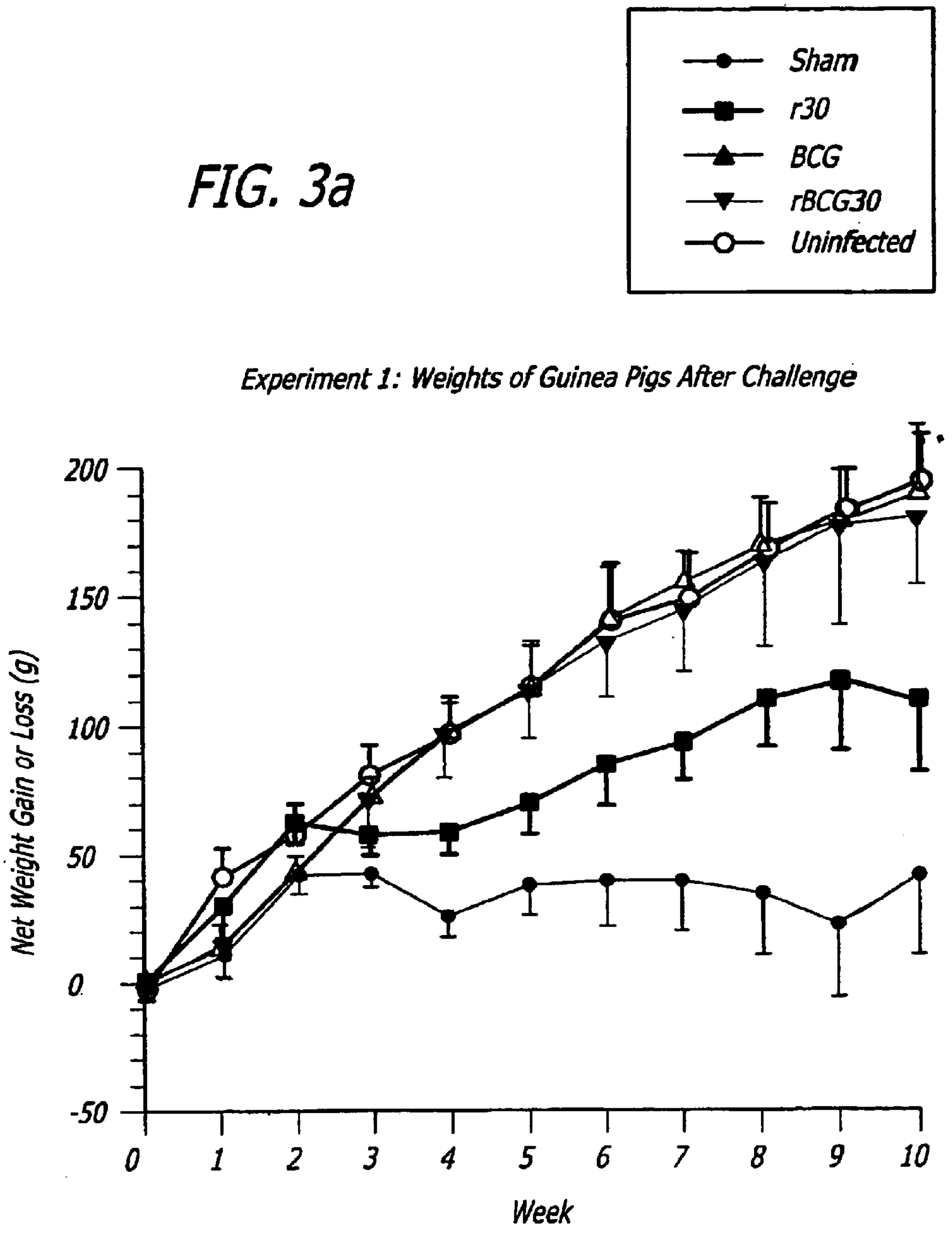
FIG. 3 graphically depicts the weight change in guinea pigs labeled 3*a* and 3*b* following post immunization challenge with *M. tuberculosis.*
Figure 3B:
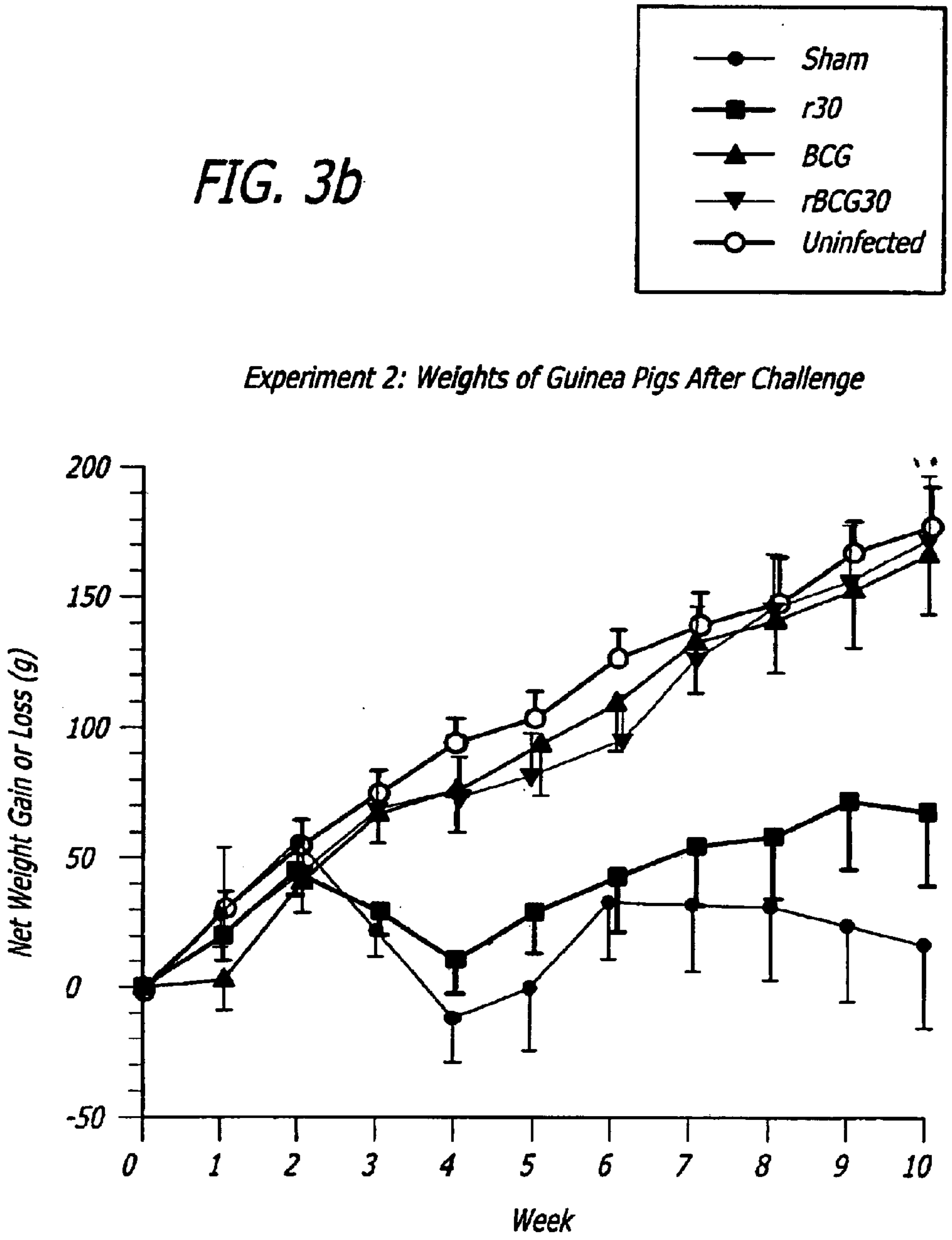

In each of the two experiments, uninfected controls gained weight normally after challenge as did animals immunized with either rBCG30 or wild-type BCG (FIG. 3). Indeed there were no significant differences in weight gain among these three groups. In contrast, sham-immunized animals and to a lesser extent r30 immunized animals, exhibited diminished weight gain over the course of the experiment (Table 2 and FIG. 3). Hence, after challenge with *M. tuberculosis*, both BCG and rBCG30 protected animals completely from weight loss, a major physical sign of tuberculosis in humans, and a hallmark of tuberculosis in the guinea pig model of this chronic infectious disease.

Figure 4A:
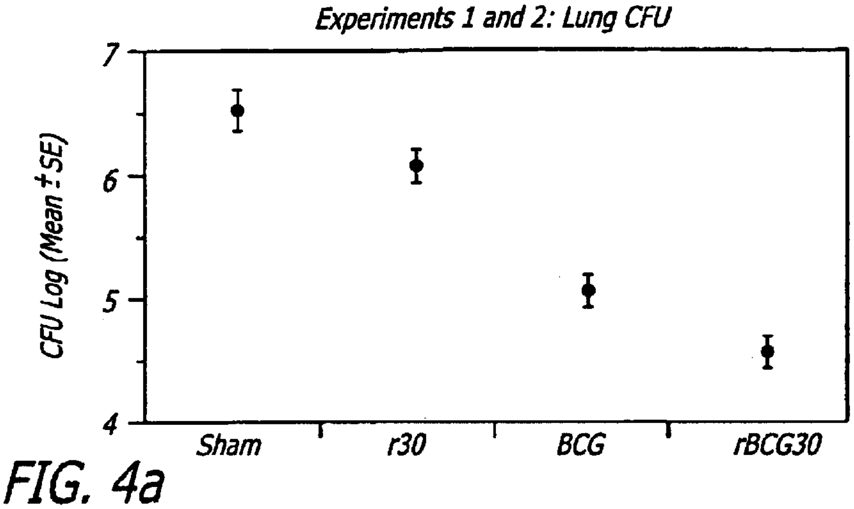
FIG. 4*a* graphically depicts Colony Forming Units (CFU) of infectious *M. tuberculosis* recovered from guinea pigs' lungs following post immunization challenge with *M. tuberculosis.*
Figure 4B:
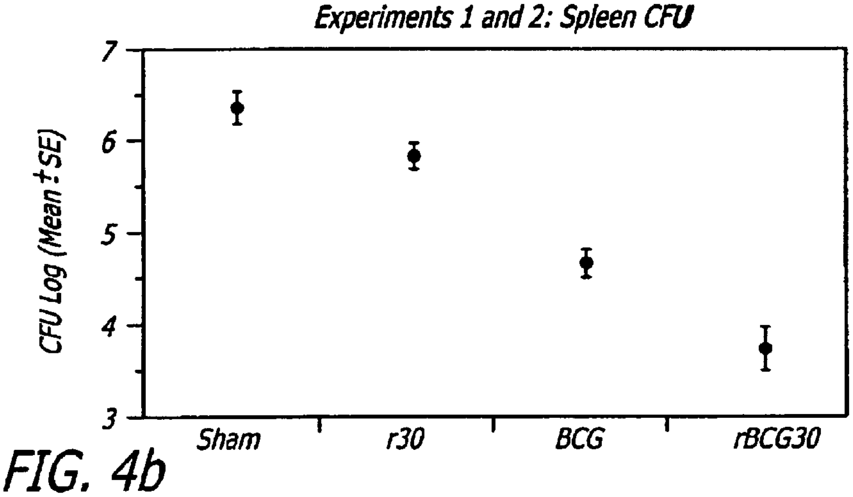
FIG. 4*b* graphically depicts Colony Forming Units (CFU) of infectious *M. tuberculosis* recovered from guinea pigs' spleens following post immunization challenge with *M. tuberculosis.*

In each of the two experiments, at the end of the 10 week observation period, guinea pigs were euthanized and the right lung and spleen of each animal was removed aseptically and assayed for CFU of *M. tuberculosis*. Sham-immunized animals had the highest bacterial load in the lungs and spleen (Table 3 and FIG. 4*a* and FIG. 4*b*). Animals immunized with r30 had fewer organisms in the lungs and spleen than the sham-immunized animals; BCG-immunized animals had fewer organisms than r30-immunized animals; and remarkably, rBCG30-immunized animals had fewer organisms than BCG-immunized animals. Statistical tests employing two way factorial analysis of variance methods to compare means demonstrated that the means of the four "treatment" groups (Sham, r30, BCG, and rBCG30) in Experiment 1 were not significantly different from the means of the four treatment groups in Experiment 2 and that it was therefore appropriate to combine the data in the two experiments. The combined data is shown in Table 4 and FIG. 3. Of greatest interest and importance, the rBCG30-immunized animals had 0.5 log fewer organisms in the lungs and nearly 1 log fewer organisms in the spleen than BCG-immunized animals. On statistical analysis, employing analysis of variance methods to compare means and the Tukey-Fisher least significant difference (LSD) criterion to assess statistical significance, the mean of each of the four groups in both the lungs and spleens was significantly different from the mean of each of the others (Table 4). Differences between the rBCG30 and BCG immunized animals in the lungs were significant at $p=0.02$ and in the spleens at $p=0.001$. Paralleling the differences in CFU in the lungs, on gross inspection, lungs of rBCG30-immunized animals had less lung destruction than BCG-immunized animals (20±4% versus 35±5% mean±SE).

Thus, administration of recombinant BCG expressing the *M. tuberculosis* 30 kDa major extracellular non-fusion protein induced high level protection against aerosol challenge with *M. tuberculosis* in the highly susceptible guinea pig model of pulmonary tuberculosis. In contrast, as described in the examples below, administration of the same mycobacterial extracellular non-fusion protein (the *M. tuberculosis* recombinant 30 kDa major extracellular non-fusion protein) in adjuvant in combination with BCG does not induce high level protection against aerosol challenge with *M. tuberculosis*; nor does administration of recombinant *M. smegmatis* expressing the *M. tuberculosis* 30 kDa major extracellular non-fusion protein; nor does administration of the *M. tuberculosis* 30 kDa major extracellular non-fusion protein in microspheres that are of the same approximate size as BCG and like BCG slowly release the proteins over 60–90 days; nor does administration of the *M. tuberculosis* 30 kDa major extracellular non-fusion protein encapsulated in liposomes.

A very surprising aspect of this invention is that the rBCG30 strain induced protection superior to wild-type BCG even though the wild-type expresses and secretes an endogenous highly homologous 30 kDa major extracellular protein. (See FIG. 1). The gene encoding the 30 kDa protein from substrain BCG Connaught has not been sequenced. However, the sequence of the 30 kDa protein of two other substrains of BCG, deduced from the sequence of the cloned gene of these substrains, differs from the *M. tuberculosis* protein by only one amino acid (BCG Paris 1173 P2) or by 5 amino acids including two additional amino acids (BCG Tokyo). (See pages 3041–3042 of Harth, G., B. -Y. Lee, J. Wang, D. L. Clemens, and M. A. Horwitz. 1996. Novel insights into the genetics, biochemistry, and immunocytochemistry of the 30-kilodalton major extracellular protein of *Mycobacterium tuberculosis*. Infect. Immun. 64:3038–3047 the entire contents of which are herein incorporated by reference). Hence, the improved protection of the recombinant strain is unlikely to be due to the small amino acid difference between the recombinant and endogenous proteins. More likely, it is due to the enhanced expression of the recombinant non-fusion protein compared with the endogenous protein. If so, then the abundant expression obtained by using a high copy number plasmid was likely an important factor in the success of the recombinant immunogenic composition.

In a third experiment, specific-pathogen free 250–300 g outbred male Hartley strain guinea pigs from Charles River Breeding Laboratories, in groups of 9, were immunized intradermally with $10^3$ CFU of one of the following strains:

| | |
|---|---|
| Group A: | BCG Tice Parental Control |
| Group B: | rBCG30 Tice I (pSMT3-MTB30) |
| Group C: | rBCG30 Tice II (pNBV1-pglnA1-MTB30) |
| Group D: | rBCG23.5 Tice I (pNBV1-pglnA1-MTB23.5) |
| Group E: | rBCG30/23.5 Tice I (pNBV1-pglnA1-MTB30/23.5) |
| Group F: | rBCG30 Tice II (pNBV1-pglnA1-MTB30) and rBCG23.5 Tice I (pNBV1-pglnA1-MTB23.5) ($5 \times 10^2$ of each strain). |

In addition, 18 animals were sham immunized with buffer only as follows: Group G: 12 sham animals (for subsequent challenge only) and Group H: 6 sham animals (for skin testing only).

Nine weeks after immunization, 9 guinea pigs in each Group A–F above and the 6 animals in the sham Group H were shaved over the back and injected intradermally with 10 $\mu$g of purified recombinant *M. tuberculosis* 30 kDa major extracellular protein (r30) in 100 $\mu$l phosphate buffered saline. Animals immunized with a strain expressing r23.5 (Groups A, D, E, F) and the 6 sham animals in Group H were additionally skin-tested with 10 $\mu$g of purified recombinant *M. tuberculosis* 23.5 kDa major extracellular protein in 100 $\mu$l phosphate buffered saline. After 24 h, the diameter of erythema and induration was measured. (A separate group of sham-immunized animals from the one used in the challenge studies was used for skin-testing. Sham-immunized animals used in challenge studies were not skin-tested to eliminate the possibility that the skin-test itself might influence the outcome).

The results, as summarized in Table 9, show that the animals immunized with the parental BCG Tice strain (Group A) and the sham-immunized animals (Group H) had little or no erythema and induration upon testing with r30 or r23.5. In contrast, animals immunized with a recombinant BCG strain expressing r30 had marked erythema and induration in response to r30 that was significantly higher than in the BCG Tice or sham immunized animals. Similarly, animals immunized with the recombinant BCG strain expressing r23.5 had marked erythema and induration in response to r23.5 that was significantly higher than in the BCG Tice or sham immunized animals. Moreover, animals immunized with the recombinant BCG strain expressing both r30 and r23.5 had marked erythema and induration in response to both of these proteins that was significantly higher than in the BCG Tice or sham immunized animals. Finally, animals immunized with two different strains of recombinant BCG at the same time, one expressing r30 and the other expressing r23.5, had marked erythema and induration in response to both of these proteins that was significantly higher than in the BCG Tice or sham immunized animals.

Interestingly, animals immunized with the new recombinant BCG strains (Groups C, D, E, and F), all of which express the recombinant proteins utilizing a promoter derived from the upstream region of the *M. tuberculosis* glnA1 gene, did not have greater erythema and induration to r30 than animals immunized with the rBCG30 Tice I strain, that expresses r30 utilizing a promoter derived from the upstream region of the *M. tuberculosis* gene encoding the 30 kDa major extracellular protein.

Nine weeks after immunization and immediately after skin-testing, all animals in Groups A–G were challenged with an aerosol generated from a 10 ml single-cell suspension containing $5\times10^4$ colony-forming units (CFU) of *M. tuberculosis*. (Prior to challenge, the challenge strain, *M. tuberculosis* Erdman strain [ATCC 35801], had been passaged through outbred guinea pigs to maintain virulence, cultured on 7H11 agar, subjected to gentle sonication to obtain a single cell suspension, and frozen at −70° C.). This aerosol dose delivered ~20 live bacilli to the lungs of each animal. The airborne route of infection was used because this is the natural route of infection for pulmonary tuberculosis. A large dose was used so as to induce measurable clinical illness in 100% of control animals within a relatively short time frame (10 weeks). Afterwards, guinea pigs were individually housed in stainless steel cages contained within a laminar flow biohazard safety enclosure and allowed free access to standard laboratory chow and water. The animals were observed for illness and weighed weekly for 10 wk and then euthanized. The right lung and spleen of each animal was removed and cultured for CFU of *M. tuberculosis* on Middlebrook 7H11 agar for two weeks at 37° C., 5%$CO_2$-95% air atmosphere.

The results of the assay for CFU in the lungs and spleens are shown in Table 10. These results showed that animals immunized with BCG or any recombinant BCG strain had much lower CFU in the lungs and spleens than the sham immunized animals. Of importance, animals immunized with any of the recombinant BCG strains had lower CFU in the lungs and spleens than animals immunized with the parental BCG Tice strain. However, none of the recombinant strains tested in this experiment were superior to rBCG30 Tice I.

In a fourth experiment, specific-pathogen free 250–300 g outbred male Hartley strain guinea pigs from Charles River Breeding Laboratories, in groups of 6, were immunized intradermally with 103 CFU of one of the following strains:

| | |
|---|---|
| Group I: | BCG Tice Parental Control |
| Group J: | rBCG30 Tice I (pSMT3-MTB30) |
| Group K: | rBCG30 Tice III (pNBV1-MTB30) |
| Group L: | rBCG23.5 Tice II (pNBV1-pMTB23.5) |
| Group M: | rBCG30/23.5 Tice IIA (pNBV1-MTB30/23.5↑↑) |
| Group N: | rBCG30/23.5 Tice IIB (pNBV1-MTB30/23.5↑↓) |
| Group O: | rBCG32A Tice I (pNBV1-MTB32A). |
| Group P | Sham immunized with buffer only (six animals). |

Nine weeks after immunization, guinea pigs in Groups I–P above were shaved over the back. Animals immunized with a strain expressing r30 (Groups I, J, K, M, and N) and the 6 sham immunized animals in Group P were injected intradermally with 10 $\mu$g of purified recombinant *M. tuberculosis* 30 kDa major extracellular protein (r30) in 100 $\mu$l phosphate buffered saline. Animals immunized with a strain expressing r23.5 (Groups L, M, N) and the 6 sham animals in Group P were skin-tested with 10 $\mu$g of purified recombinant *M. tuberculosis* 23.5 kDa major extracellular protein in 100 $\mu$l phosphate buffered saline. Animals injected with a strain expressing r32A (Group O) and the 6 sham animals in Group P were skin-tested with 10 $\mu$g of purified recombinant *M. tuberculosis* 32A kDa major extracellular protein in 100 $\mu$l phosphate buffered saline. After 24 h, the diameter of erythema and induration was measured.

The results, as summarized in Table 11, show that the animals immunized with the parental BCG Tice strain (Group A) had no erythema and induration upon testing with r30, whereas animals (Groups J, K, M, N) immunized with strains expressing the recombinant 30 kDa protein had marked erythema and induration. Moreover, animals (Groups K, M, and N) immunized with strains expressing r30 in greater abundance than rBCG30 Tice I and utilizing a promoter derived from the upstream region of the 30 kDa protein gene had greater induration, a more reliable indicator of cutaneous delayed-type hypersensitivity than erythema, than animals immunized with rBCG30 Tice I. Animals (Groups L, M, and N) immunized with a recombinant BCG strain expressing r23.5, a protein absent in the parental BCG strain, had marked erythema and induration in response to r23.5, whereas sham immunized animals had little erythema and no induration in response to r23.5 The animals (Group 0) immunized with a recombinant BCG strain overexpressing r32A had much greater erythema and induration in response to the 32A kDa protein than sham-immunized animals.

Figure 6:
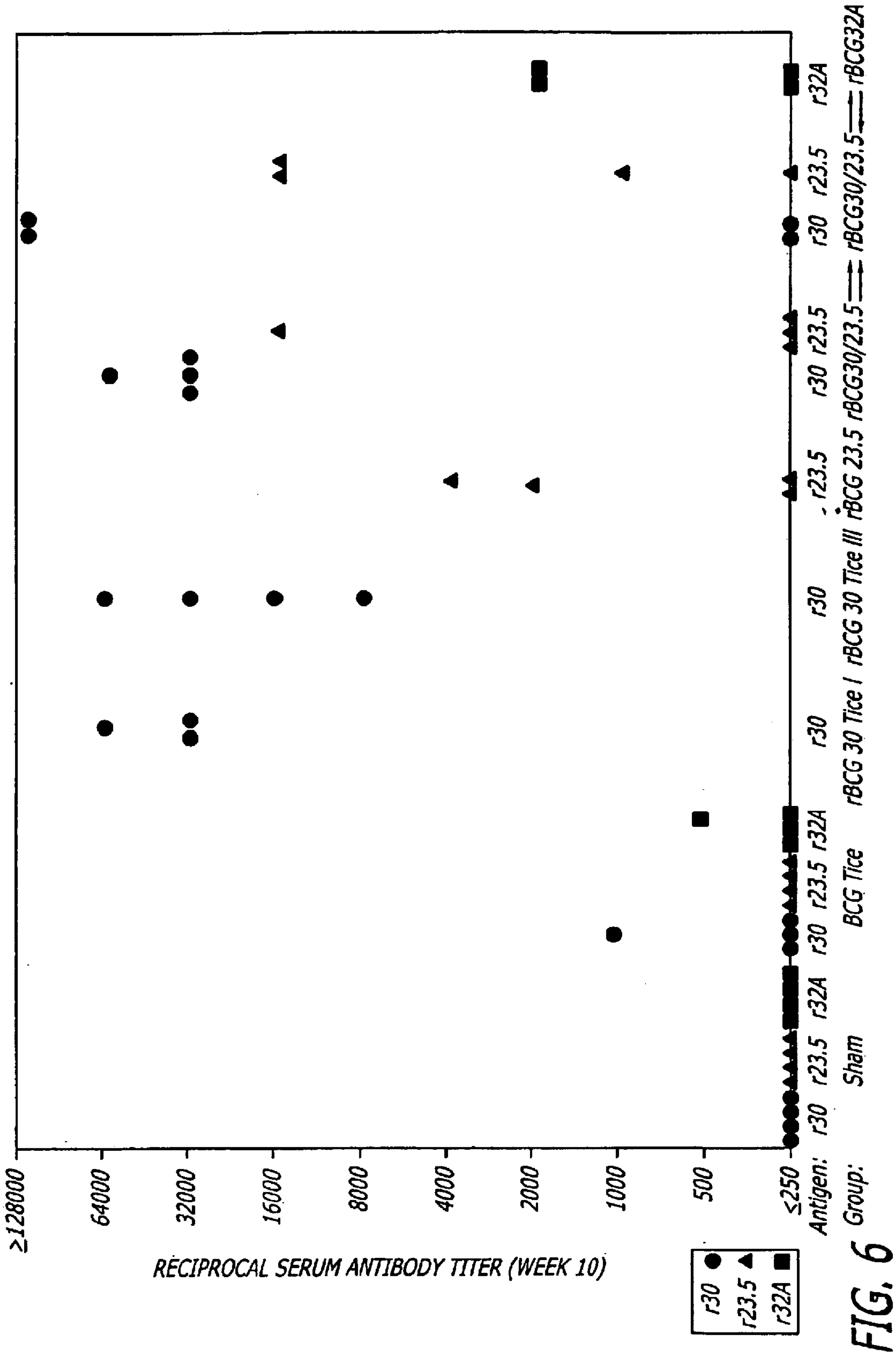
FIG. 6 graphically depicts antibody titers to purified recombinant *M. tuberculosis* 30 kDa major extracellular protein (r30), 32A kDa major extracellular protein (r32A) and 23.5 kDa major extracellular protein (r 23.5).

Additionally, ten weeks after immunization, blood was obtained from several guinea pigs in Groups I-P and serum antibody titers were determined to purified recombinant *M. tuberculosis* 30 kDa Major Extracellular Protein (r30), 32A kDa Major Extracellular Protein (r32A) and 23.5 kDa Major Extracellular Protein (r23.5). Antibody titers were assayed by ELISA and the reciprocal antibody titers for each animal determined. FIG. 6 graphically depicts these results.

In a fifth experiment designed to demonstrate protection from infection in immunized mammals specific-pathogen free 250–300 g outbred male Hartley strain guinea pigs from Charles River Breeding Laboratories, in groups of 6, were immunized intradermally with $10^3$ CFU of one of the following strains:

| | |
|---|---|
| Group I: | BCG Tice Parental Control |
| Group J: | rBCG30 Tice I (pSMT3-MTB30) |
| Group K: | rBCG30 Tice III (pNBV1-MTB30) |
| Group L: | rBCG23.5 Tice II (pNBV1-pMTB23.5) |
| Group M: | rBCG30/23.5 Tice IIA (pNBV1-MTB30/23.5↑↑) |
| Group N: | rBCG30/23.5 Tice IIB (pNBV1-MTB30/23.5↑↓) |
| Group O: | rBCG32A Tice I (pNBV1-MTB32A) |
| Group P: | 12 sham animals immunized with antigen-free buffer. |

Nine weeks after immunization and immediately after skin-testing, all animals in Groups I-P were challenged with an aerosol generated from a 10 ml single-cell suspension containing $5\times10^4$ colony-forming units (CFU) of *M. tuberculosis*. (Prior to challenge, the challenge strain, *M. tuberculosis* Erdman strain (ATCC 35801), had been passaged through outbred guinea pigs to maintain virulence, cultured on 7H11 agar, subjected to gentle sonication to obtain a single cell suspension, and frozen at −70° C.). This aerosol dose delivered ~20 live bacilli to the lungs of each animal. The airborne route of infection was used because this is the natural route of infection for pulmonary tuberculosis. A large dose was used so as to induce measurable clinical illness in s100% of control animals within a relatively short time frame (10 weeks). Afterwards, guinea pigs were individually housed in stainless steel cages contained within a laminar flow biohazard safety enclosure and allowed free access to standard laboratory chow and water. The animals were observed for illness and weighed weekly for 10 wk and then euthanized. The right lung and spleen of each animal was removed and cultured for CFU of *M. tuberculosis*. The results are shown in Table 12 below.

TABLE 1

Cutaneous Delayed Type Hypersensitivity to the *M. tuberculosis* 30 kDa Major Extracellular Protein

| | Erythema (Mean Diameter ± SE) (mm) | Induration (Mean Diameter ± SE) (mm) |
|---|---|---|
| Experiment 1 | | |
| Sham-immunized | 0.0 ± 0.0 | 1.0 ± 0.0 |
| r30 | 15.0 ± 1.2 | 4.2 ± 0.3 |
| BCG | 0.8 ± 0.8 | 1.7 ± 0.2 |
| rBCG30 | 19.8 ± 2.2 | 3.1 ± 0.2 |
| Experiment 2 | | |
| Sham-immunized | 0.0 ± 0.0 | 1.0 ± 0.0 |
| r30 | 15.3 ± 0.9 | 5.2 ± 0.7 |
| BCG | 3.0 ± 1.5 | 1.0 ± 0.0 |
| rBCG30 | 16.5 ± 0.9 | 2.7 ± 0.4 |

TABLE 2

Net Weight Gain After Aerosol Challenge with Virulent *M. tuberculosis* Erdman Strain

| | Week 0 (Mean Weight ± SE) (g) | Week 10 (Mean Weight ± SE) (g) | Net Weight Gain (g) Week 0–10 (Mean ± SE) |
|---|---|---|---|
| Experiment 1 | | | |
| Sham-immunized | 763.1 ± 17.1 | 805.4 ± 27.8 | 42.3 ± 28.2 |
| r30 | 793.8 ± 21.6 | 906.3 ± 44.6 | 112.6 ± 32.0 |
| BCG | 763.8 ± 28.7 | 956.3 ± 45.4 | 192.5 ± 23.7 |
| rBCG30 | 767.8 ± 17.6 | 947.7 ± 31.3 | 179.9 ± 25.1 |
| Experiment 2 | | | |
| Sham-immunized | 839.1 ± 21.7 | 857.6 ± 32.4 | 18.5 ± 30.9 |
| r30 | 801.9 ± 36.3 | 888.6 ± 39.7 | 86.7 ± 28.3 |
| BCG | 796.6 ± 29.8 | 963.6 ± 19.8 | 167.0 ± 23.3 |
| rBCG30 | 785.7 ± 17.7 | 958.7 ± 27.7 | 173.0 ± 24.9 |

TABLE 3

Colony Forming Units (CFU) of *M. tuberculosis* in Lungs and Spleens of Animals Challenged by Aerosol with *M. tuberculosis* Erdman Strain Combined Experiments 1 and 2

| | n | Lung CFU $Log_{10}$ (Mean ± SE) | Spleen CFU $Log_{10}$ (Mean ± SE) |
|---|---|---|---|
| Sham-immunized | 18 | 6.47 ± 0.17 | 6.27 ± 0.19 |
| r30 | 18 | 6.02 ± 0.14 | 5.73 ± 0.14 |
| BCG | 17 | 5.00 ± 0.13 | 4.57 ± 0.17 |
| rBCG30 | 18 | 4.53 ± 0.14 | 3.65 ± 0.25 |

TABLE 4

Summary of Statistical Analysis (ANOVA) CFU in Lungs and Spleen Combined Experiments 1 and 2

| | | |
|---|---|---|
| Lung | Sham vs. r30 | p = 0.03 |
| | r30 vs. BCG | p = 0.0001 |
| | BCG vs. rBCG30 | p = 0.02 |
| Spleen | Sham vs. r30 | p = 0.05 |
| | r30 vs. BCG | p = 0.0001 |
| | BCG vs. rBCG30 | p = 0.001 |

TABLE 5

Colony Forming Units (CFU) of *M. tuberculosis* in Lungs and Spleens of Animals Challenged by Aerosol with *M. tuberculosis* Erdman Strain: Animals Immunized with BCG or with BCG plus Recombinant *M. tuberculosis* 30 kDa Protein in Adjuvant or Sham-immunized

| | n | Lung CFU $Log_{10}$ (Mean ± SE) | Spleen CFU $Log_{10}$ (Mean ± SE) |
|---|---|---|---|
| Sham-immunized | 17 | 6.40 ± 0.18 | 5.65 ± 0.20 |
| BCG | 8 | 4.70 ± 0.13 | 2.91 ± 0.35 |
| BCG ± r30 | 9 | 5.30 ± 0.23 | 3.34 ± 0.37 |

TABLE 6

Colony Forming Units (CFU) of *M. tuberculosis* in Lungs and Spleens of Animals Challenged by Aerosol with *M. tuberculosis* Erdman Strain: Animals Immunized with Live Recombinant *M. smegmatis* Expressing the *M. tuberculosis* 30 kDa Major Extracellular Protein (r*M. smegmatis*30)

| | n | Lung CFU $Log_{10}$ (Mean ± SE) | Spleen CFU $Log_{10}$ (Mean ± SE) |
|---|---|---|---|
| Sham-immunized | 9 | 6.63 ± 0.27 | 6.34 ± 0.29 |
| BCG | 8 | 4.61 ± 0.14 | 4.31 ± 0.27 |
| *M. smegmatis* Control | 9 | 5.92 ± 0.31 | 5.29 ± 0.34 |
| r*M. smegmatis*30 | 9 | 5.48 ± 0.26 | 5.55 ± 0.28 |

TABLE 7

Colony Forming Units (CFU) of *M. tuberculosis* in Lungs and Spleens of Animals Challenged by Aerosol with *M. tuberculosis* Erdman Strain: Animals Immunized with Microspheres That are of the Same Approximate Size as BCG and Like BCG Slowly Release the *M. tuberculosis* 30 kDa Major Extracellular Protein (r30)
Animals Immunized with Liposomes That Contain the *M. tuberculosis* 30 kDa Major Extracellular Protein (r30)

| | n | Lung CFU $Log_{10}$ (Mean ± SE) | Spleen CFU $Log_{10}$ (Mean ± SE) |
|---|---|---|---|
| Sham-immunized | 9 | 6.31 ± 0.19 | 6.20 ± 0.26 |
| BCG | 9 | 5.35 ± 0.14 | 4.81 ± 0.21 |
| rBCG30 | 9 | 4.48 ± 0.14 | 3.73 ± 0.33 |
| Control Microspheres | 9 | 6.67 ± 0.29 | 5.94 ± 0.32 |
| Microspheres with r30 (10 mg × 1) | 6 | 6.10 ± 0.32 | 5.93 ± 0.41 |
| Microspheres with r30 (3.3 mg × 3) | 9 | 6.42 ± 0.17 | 6.04 ± 0.28 |
| Control Liposomes | 9 | 6.24 ± 0.23 | 6.41 ± 0.21 |
| Liposomes with r30 | 9 | 5.77 ± 0.18 | 5.63 ± 0.16 |

TABLE 8

Expression of recombinant proteins by recombinant strains of BCG Tice

| Strain | Expression of 30 kDa Protein (Relative Units) | Expression of 23.5 kDa Protein (mg/L) | Expression of 32A kDa Protein (Relative Units) |
|---|---|---|---|
| BCG Tice | 1.0 | 0 | 1.0 |
| rBCG30 Tice I | 5.4x | | |
| rBCG30 Tice II (pNBV1-pglnA1-MTB30) | 24x | | |
| rBCG23.5 Tice I (pNBV1-pglnA1-MTB23.5) | | Approximately 10–15 mg/L | |
| rBCG30/23.5 Tice II (pNBV1-pglnA1-MTB30/23.5) | 24x | Approximately 10–15 mg/L | |

TABLE 8-continued

Expression of recombinant proteins by recombinant strains of BCG Tice

| Strain | Expression of 30 kDa Protein (Relative Units) | Expression of 23.5 kDa Protein (mg/L) | Expression of 32A kDa Protein (Relative Units) |
|---|---|---|---|
| rBCG30 Tice III (pNBV1-MTB30) | 14.4x | | |
| rBCG23.5 Tice II (pNBV1-MTB23.5) | | 16.2 mg/L | |
| rBCG30/23.5 Tice IIA (pNBV1-MTB30/23.5↑↑) | 23.3x | 18.7 mg/L | |
| rBCG30/23.5 Tice IIB (pNBV1-MTB30/23.5↑↓) | 25.7x | 16.6 mg/L | |
| rBCG32A Tice I (pNBV1-MTB32A) | | | 10.5x |
| rBGG(MB)30 Tice (pNBV1-MB30) | 9.7x | | |
| rBCG(ML)30 Tice I (pNBV1-ML30) | 9.7x | | |

TABLE 9

Cutaneous Delayed-type Hypersensitivity (DTH) to Purified Recombinant *M. tuberculosis* 30 kDa Major Extracellular Protein (r30) and 23.5 kDa Major Extracellular Protein (r23.5).

| Group | Strain | Test Antigen | Erythema (mm ± SE) | Induration (mm ± SE) |
|---|---|---|---|---|
| A | BCG Tice | r30 | 0 ± 0 | 0 ± 0 |
| | | r23.5 | 0 ± 0 | 0 ± 0 |
| B | rBCG30 Tice I | r30 | 16.0 ± 2.3 | 9.0 ± 1.9 |
| C | rBCG30 Tice II | r30 | 15.2 ± 1.2 | 11.2 ± 1.0 |
| D | rBCG23.5 Tice I | r23.5 | 11.3 ± 2.3 | 8.7 ± 1.7 |
| E | rBCG30/23.5 Tice I | r30 | 13.6 ± 2.1 | 12.4 ± 1.8 |
| | | r23.5 | 10.3 ± 2.9 | 7.3 ± 2.8 |
| F | rBCG30 Tice II + | r30 | 9.9 ± 2.6 | 8.5 ± 2.6 |
| | rBCG23.5 Tice I | r23.5 | 7.6 ± 2.2 | 5.6 ± 2.2 |
| H | Sham | r30 | 0 ± 0 | 0 ± 0 |
| | | r23.5 | 0 ± 0 | 0 ± 0 |

TABLE 10

Protective Immunity to Aerosol Challenge: CFU in Lungs and Spleens

| Group | Strain | Lung (Mean Log CFU ± SE) | Spleen (Mean Log CFU ± SE) |
|---|---|---|---|
| A | BCG Tice | 4.89 ± 0.14 | 3.92 ± 0.24 |
| B | rBCG30 Tice I | 4.33 ± 0.18 | 2.99 ± 0.25 |
| C | rBCG30 Tice II | 4.61 ± 0.12 | 3.14 ± 0.19 |
| D | rBCG23.5 Tice I | 4.70 ± 0.15 | 3.40 ± 0.20 |
| E | rBCG30/23.5 Tice I | 4.86 ± 0.17 | 3.60 ± 0.26 |
| F | rBCG30 Tice II + rBCG23.5 Tice I | 4.65 ± 0.20 | 3.80 ± 0.25 |
| G | Sham | 6.20 ± 0.33 | 6.10 ± 0.33 |

TABLE 11

Cutaneous Delayed-type Hypersensitivity (DTH) to Purified Recombinant *M. tuberculosis* 30 kDa Major Extracellular Protein (r30) and 23.5 kDa Major Extracellular Protein (r23.5)

| Group | Strain | Test Antigen | Erythema (mm ± SE) | Induration (mm ± SE) |
|---|---|---|---|---|
| I | BCG Tice | r30 | 0 ± 0 | 0 ± 0 |
| J | rBCG30 Tice I | r30 | 25.1 ± 2.8 | 10.7 ± 3.0 |
| K | rBCG30 Tice III | r30 | 24.6 ± 2.5 | 22.3 ± 2.3 |
| L | rBCG23.5 Tice II | r23.5 | 10.9 ± 3.5 | 10.8 ± 3.4 |
| M | rBCG30/23.5 Tice IIA | r30 | 18.0 ± 3.9 | 16.4 ± 3.8 |
| | | r23.5 | 9.3 ± 1.9 | 8.6 ± 1.9 |
| N | rBCG30/23.5 Tice IIB | r30 | 16.5 ± 3.7 | 14.4 ± 3.3 |
| | | r23.5 | 9.0 ± 2.3 | 9.0 ± 2.3 |
| O | rBCG32A I | r32A | 7.8 ± 1.1 | 5.3 ± 1.8 |
| P | Sham | r30 | 5.6 ± 3.7 | 4.4 ± 3.4 |
| | | r23.5 | 2.8 ± 1.3 | 0 ± 0 |
| | | 32A | 0.8 ± 0.5 | 0 ± 0 |

TABLE 12

Protective Immunity to Aerosol Challenge: CFU in Lungs and Spleens

| Group | Strain | Lung (Mean Log CFU ± SE) | Spleen (Mean Log CFU ± SE) |
|---|---|---|---|
| I | BCG Tice | 4.80 ± 0.12 | 3.60 ± 0.18 |
| J | rBCG30 Tice I | 4.15 ± 0.13 | 2.36 ± 0.22 |
| K | rBCG30 Tice III | 3.80 ± 0.35 | 2.74 ± 0.31 |
| L | rBCG23.5 Tice II | 4.49 ± 0.23 | 3.08 ± 0.24 |
| M | rBCG30/23.5 Tice IIA | 4.88 ± 0.12 | 3.12 ± 0.27 |
| N | rBCG30/23.5 Tice IIB | 5.01 ± 0.10 | 3.25 ± 0.29 |
| O | rBCG32A Tice I | 4.93 ± 0.09 | 3.28 ± 0.10 |
| P | Sham | 6.09 ± 0.12 | 5.91 ± 0.11 |

The following Examples serve to illustrate the novel aspect of the present invention. Each example illustrates a means of delivering the immunogens of the present invention using techniques closely related to, but different from the immunogenic composition of the present invention. Specifically, Example 1 demonstrates that when the immunogens of the present invention are administered with, but not expressed in vivo by BCG, a high level of protective immunity is not achieved.

Example 2 demonstrates that the in vivo expression of the immunogens of the present invention using a *Mycobacterium* sp. closely related to BCG, but unable to replicate in mammalian hosts, fails to induce significant levels of protection against challenge with *M. tuberculosis*. Examples 3 and 4 demonstrate that the slow release of the immunogens of the present invention by synthetic immunogenic composition microcarriers also fails to induce significant levels of protection against challenge with *M. tuberculosis.*

Example 5 provides a representative method for administering the auxotrophic embodiments of the present invention. Similarly, Example 6 details the use of non-auxotrophic attenuated strains of the present invention.

EXAMPLES

Therefore, the following Examples serve to highlight the completely surprising and remarkable advance that the intracellular pathogen immunogenic compositions of the present invention represent to the field of infectious disease immunology. These Examples are for illustrative purposes only and are not to be deemed limiting.

Example 1

Immunization of guinea pigs with BCG plus recombinant *M. tuberculosis* 30 kDa major extracellular protein (r30) does not induce high level protection against challenge with *M. tuberculosis.*

Figure 5:
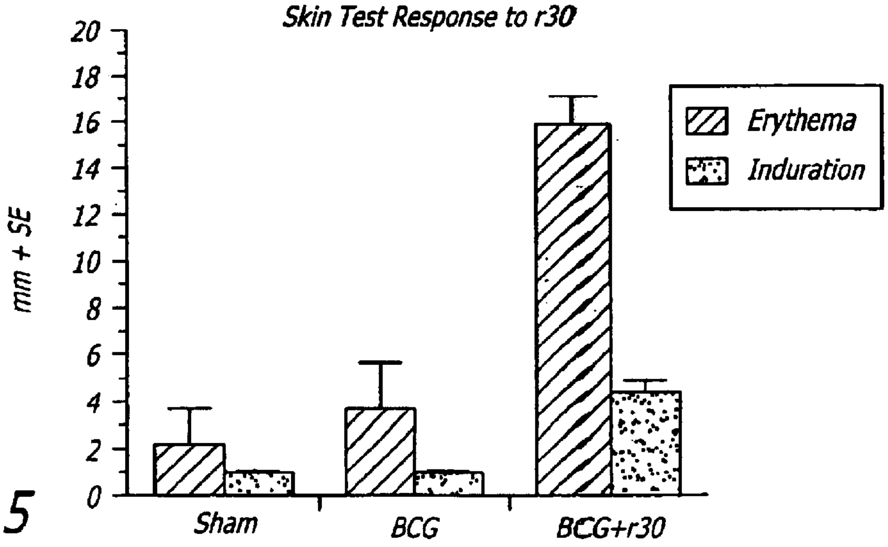
FIG. 5 graphically depicts the skin test response of guinea pigs to sham immunogenic composition, BCG alone and BCG administered with recombinant 30 kDa of *M. tuberculosis.*

We previously immunized guinea pigs with BCG plus r30 in a powerful adjuvant (SAF, Syntex Adjuvant Formulation). The r30 protein (100 μg per immunization) was administered intradermally three times. This induced a strong cutaneous delayed-type hypersensitivity (C-DTH) response to r30 (FIG. 5). Indeed, the C-DTH response was comparable to that induced by recombinant BCG expressing r30. Nevertheless, immunization with both BCG and r30 did not induce high level protection against challenge with *M. tuberculosis* (Table 5). Animals immunized with both BCG and r30 did not have lower levels of CFU in the lungs and spleen than animals immunized with BCG alone. This result is in direct contrast to the result described above in which animals immunized with recombinant BCG expressing r30 exhibited high level protection when challenged with *M. tuberculosis.*

Example 2

Immunization of guinea pigs with live recombinant *M. smegmatis* expressing the *M. tuberculosis* 30 kDa major extracellular protein (r30) in a form indistinguishable from the native form does not induce high level protection against challenge with *M. tuberculosis.*

In one of the same experiments in which we immunized animals with BCG, we immunized guinea pigs with live recombinant *M. smegmatis* expressing the *M. tuberculosis* 30 kDa major extracellular protein (r30) in a form indistinguishable from the native form. The expression and secretion of the *M. tuberculosis* 30 kDa major extracellular protein (r30) by *M. smegmatis* was equal to or greater than that of the recombinant BCG strain expressing and secreting the *M. tuberculosis* 30 kDa major extracellular protein. Moreover, the dose of recombinant *M. smegmatis,* $10^9$ bacteria, was very high, one million times the dose of recombinant BCG ($10^3$ bacteria), to more than compensate for the poor multiplication of *M. smegmatis* in the animal host. To compensate even further, the recombinant *M. smegmatis* was administered three times intradermally, whereas the recombinant BCG was administered only once intradermally. Immunization with recombinant *M. smegmatis* expressing the r30 protein induced a strong cutaneous delayed-type hypersensitivity (C-DTH) response to r30. Indeed, the C-DTH response was comparable to or greater than that induced by recombinant BCG expressing r30. Nevertheless, the live recombinant *M. smegmatis* expressing the *M. tuberculosis* 30 kDa major extracellular protein did not induce high level protection against challenge with *M. tuberculosis* (Table 6). Animals immunized with the live recombinant *M. smegmatis* expressing the *M. tuberculosis* 30 kDa major extracellular protein did not have lower levels of CFU in the lungs and spleen than animals immunized with BCG alone. This result is in direct contrast to the result described above in which animals immunized with recombinant BCG expressing r30 exhibited high level protection when challenged with *M. tuberculosis.*

Example 3

Immunization of guinea pigs with microspheres that are of the same approximate size as BCG and like BCG slowly release the *M. tuberculosis* 30 kDa major extracellular protein (r30) over 60–90 days does not induce high level protection against challenge with *M. tuberculosis.*

In one of the same experiments in which we immunized animals with rBCG30 and BCG, we immunized guinea pigs with microspheres that are of the same approximate size as BCG and like BCG slowly release the *M. tuberculosis* 30 kDa major extracellular protein (r30) over 60–90 days. One set of animals was immunized once with microspheres containing 10 mg of r30. Another set of animals was immunized three times with microspheres containing 3.3 mg of r30. This amount was calculated to greatly exceed the amount of r30 protein expressed by the recombinant BCG strain. Immunization with either regimen of microspheres induced a strong cutaneous delayed-type hypersensitivity (C-DTH) response to r30. Indeed, the C-DTH response was comparable to that induced by recombinant BCG expressing r30. Nevertheless, immunization with the microspheres that are of the same approximate size as BCG and like BCG slowly release the *M. tuberculosis* 30 kDa major extracellular protein did not induce high level protection against challenge with *M. tuberculosis* (Table 7). Animals immunized with the microspheres did not have lower levels of CFU in the lungs and spleen than animals immunized with BCG alone. This result is in direct contrast to the result described above in which animals immunized with recombinant BCG expressing r30 exhibited high level protection when challenged with *M. tuberculosis.*

Example 4

Immunization of guinea pigs with liposomes containing the *M. tuberculosis* 30 kDa major extracellular protein does not induce high level protection against challenge with *M. tuberculosis.*

In the same experiment as in Example 3, we immunized guinea pigs with liposomes containing the *M. tuberculosis* 30 kDa major extracellular protein. The animals were immunized three times with liposomes containing 50 μg of r30. This induced a moderately strong cutaneous delayed-type hypersensitivity (C-DTH) response to r30. The C-DTH response was greater than that induced by BCG and control liposomes but less than that induced by recombinant BCG expressing r30. Nevertheless, immunization with liposomes containing the *M. tuberculosis* 30 kDa major extracellular protein did not induce high level protection against challenge with *M. tuberculosis* (Table 7). Animals immunized with the liposomes containing the *M. tuberculosis* 30 kDa major extracellular protein did not have lower levels of CFU in the lungs and spleen than animals immunized with BCG alone. This result is in direct contrast to the result described above in which animals immunized with recombinant BCG expressing r30 exhibited high level protection when challenged with *M. tuberculosis.*

Example 5

Use of the Growth-regulatable Auxotrophic Strains

The growth-regulatable auxotrophic vaccines will be used as follows. Immunocompromised persons will be immunized with the vaccines, for example the tryptophan auxotroph BCG strain. The person will immediately begin supplementing his or her diet with tryptophan in sufficiently high amount so that the auxotroph can multiply at normal levels and induce a high level of protective immunity to tuberculosis. In most people, the multiplication of the recombinant BCG will not cause a health problem. The organism will multiply in the tissues to modest levels and then be cleared by the immune system. However, in some immunocompromised people, disseminated disease or other problems from bacterial multiplication may develop. These people would then immediately stop the dietary supplement. In the absence of the dietary supplement, the auxotroph would rapidly die out and cease to cause a health problem.

This approach is a particularly attractive one in the developing world where medical care may not be readily available. If a person has an adverse consequence from the immunization, the person does not need to access the health care system or obtain antibiotics, which may be costly and/or not readily available. The person need only stop taking the dietary supplement—a passive rather than active intervention.

Example 6

Use of the Non-auxotrophic Attenuated Strains

These strains will be administered to immunocompromised persons in the usual way BCG vaccines are administered i.e. without any dietary supplementation.

The immunogenic compositions of the present invention represent an entirely new approach to the induction of immune responses against intracellular pathogens. Through a series of well designed experiments and thoughtful analysis, the present inventors have thoroughly demonstrated that protective immunity is only achieved when a precisely selected intracellular pathogen, or closely related species, is transformed to express recombinant extracellular proteins of the same or different intracellular pathogen in accordance with the teachings of the present invention.

The present invention can also be used to provide diagnostic, prophylactic and therapeutic benefits against multiple intracellular pathogens simultaneously. For example a recombinant attenuated intracellular immunogenic composition like *M. bovis* can be designed to expressed immuno-protective immunogens against *M: tuberculosis* and *Legionella* sp. simultaneously. Consequently, great efficiencies in delivering immunogenic compositions could be accomplished. The non-limiting examples of recombinant BCG expressing the major extracellular proteins of *M. tuberculosis* not only serve as a fully enabling embodiment of the present invention, but represent a significant advance to medicine, and humanity as a whole.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Additional References Herein Incorporated by Reference

1. Fine, P. E. M. 1989. The BCG story: Lessons from the past and implications for the future. Rev. Infect. Dis. 11 (Suppl. 2):S353–S359.
2. Colditz, G. A. T. F. Brewer, C. S. Berkey, M. E. Wilson, E. Burdick, H. V. Fineberg, and F. Mosteller. 1994. Efficacy of BCG vaccine in the prevention of tuberculosis. Meta-analysis of the published literature. JAMA 271:698–702.
3. Horwitz, M. A., G. Harth, B. J. Dillon, and S. Malesa-Galic. 2000. Recombinant BCG vaccines expressing the *Mycobacterium tuberculosis* 30 kDa major secretory protein induce greater protective immunity against tuberculosis than conventional BCG vaccines in a highly susceptible animal model. Proc. Natl. Acad. Sci. (U.S.A.) 97:13853–13858.
4. Horwitz, M. A., B. -W. E. Lee, B. J. Dillon, and G. Harth. 1995. Protective immunity against tuberculosis induced by vaccination with major extracellular proteins of *Mycobacterium tuberculosis*. Proc. Natl. Acad. Sci. (U.S.A.) 92:1530–1534.

We claim:

1. An immunogenic composition comprising:

a recombinant Bacille Calmette-Guerin (BCG) having an extrachromosomal nucleic acid sequence comprising a gene encoding for a Mycobacterial major extracellular protein selected from the group consisting of 23.5 kDa, 30 kDa, 32 kDa and combinations thereof, wherein said Mycobacterial major extracellular protein is over expressed and secreted.

2. The immunogenic composition according to claim 1 wherein said nucleic acid sequence is under the control of a promoter that is not a heat shock promoter or a stress protein promoter.

3. The immunogenic composition according to claim 1 wherein said major extracellular protein is a non-fusion protein.

4. The immunogenic composition according to claim 1 wherein said extrachromosomal nucleic acid sequence comprises a genetic construct having genes encoding for multiple Mycobacterial major extracellular proteins wherein said genes encoding for said Mycobacterial major extracellular proteins are orientated in the same direction relative to each other within the genetic construct.

5. The immunogenic composition according to claim 1 wherein said extrachromosomal nucleic acid sequence comprises a genetic construct having genes encoding for multiple Mycobacterial major extracellular proteins wherein said genes encoding for said Mycobacterial major extracellular proteins are orientated in opposite directions relative to each other within the genetic construct.

6. The immunogenic compositions according to any one of claims 1–5 wherein said Mycobacterial major extracellular proteins are from a species of *Mycobacterium* selected from the group consisting of *Mycobacterium tuberculosis* (Mtb), *Mycobacterium bovis* (MB), and *Mycobacterium leprae* (ML).

7. An immunogenic composition comprising:

a recombinant BCG having an extrachromosomal nucleic acid sequence comprising a gene encoding for *Mycobacterium tuberculosis* 23.5 kDa major extracellular non-fusion protein under the control of a promoter wherein said promoter is not a heat shock promoter or stress protein promoter and wherein said 23.5 kDa major extracellular non-fusion protein is over expressed and secreted such that an immune response is induced in a mammal.

8. An immunogenic composition comprising:

a recombinant BCG having an extrachromosomal nucleic acid sequence comprising a gene encoding for *Mycobacterium tuberculosis* 32A kDa major extracellular non-fusion protein under the control of a promoter wherein said promoter is not a heat shock promoter or stress protein promoter and wherein said 32A kDa major extracellular non-fusion protein is over expressed and secreted such that an immune response is induced in a mammal.

9. An immunogenic composition comprising:

a recombinant Bacille Calmette-Guérin (BCG) having an extrachromosomal nucleic acid sequence comprising a genetic construct having at least one gene encoding for a *Mycobacterium tuberculosis* (Mtb) 30 kDa major extracellular non-fusion protein and an Mtb 23.5 kDa major extracellular non-fusion protein, wherein said Mtb 30 kDa major extracellular non-fusion protein and said Mtb 23.5 kDa major extracellular non-fusion protein are over expressed and secreted such that an immune response is induced in a mammal.

10. An immunogenic composition comprising:

a recombinant BCG having an extrachromosomal nucleic acid sequence comprising a gene encoding for *Mycobacterium bovis* 30 kDa major extracellular protein under the control of a promoter wherein said 30 kDa major extracellular protein is over expressed and secreted such that an immune response is induced in a mammal.

11. An immunogenic composition comprising:

a recombinant BCG having an extrachromosomal nucleic acid sequence comprising a gene encoding for *Mycobacterium leprae* 30 kDa major extracellular protein under the control of a promoter wherein said 30 kDa major extracellular protein is over expressed and secreted such that an immune response is induced in a mammal.

12. An immunogenic composition comprising:

a recombinant Bacille Calmette-Guérin (BCG) having an extrachromosomal nucleic acid sequence comprising a genetic construct having at least one gene encoding for a *Mycobacterium tuberculosis* (Mtb) 30 kDa major extracellular protein and an Mtb 23.5 kDa major extracellular protein, wherein said Mtb 30 kDa major extracellular protein and said Mtb 23.5 kDa major extracellular protein are over expressed and secreted;

and wherein said genetic construct comprises a gene encoding for said Mtb 23.5 kDa extracellular protein and a gene encoding for said Mtb 30 kDa extracellular protein and wherein said genes are orientated in the same direction relative to each other within said genetic construct.

13. An immunogenic composition comprising:

a recombinant Bacille Calmette-Guérin (BCG) having an extrachromosomal nucleic acid sequence comprising a genetic construct having at least one gene encoding for a *Mycobacterium tuberculosis* (Mtb) 30 kDa major extracellular protein and an Mtb 23.5 kDa major extracellular protein, wherein said Mtb 30 kDa major extracellular protein and said Mtb 23.5 kDa major extracellular protein are over expressed and secreted;

and wherein said genetic construct comprises a gene encoding for said Mtb 23.5 kDa extracellular protein and a gene encoding for said Mtb 30 kDa extracellular protein and wherein said genes are orientated in opposite directions relative to each other within said genetic construct.

14. The immunogenic compositions according to any one of claim 7, 8, 9, 10 or 11 wherein said immune response is a protective immune response.

15. An immunogenic composition comprising:

a growth regulatable recombinant Bacille Calmette-Guérin (BCG) having an extrachromosomal nucleic acid sequence comprising a gene encoding for a Mycobacterial major extracellular protein selected from the group consisting of 23.5 kDa, 30 kDa, 32 kDa and combinations thereof, wherein said *Mycobacteria* major extraceilular protein is over expressed and secreted.

16. The immunogenic composition according to claim 15 wherein said nucleic acid sequence is under the control of a promoter that is not a heat shock promoter or a stress protein promoter.

17. The immunogenic composition according to claim 15 wherein said major extracellular protein is a non-fusion protein.

18. The immunogenic composition according to claim 15 wherein said extrachromosomal nucleic acid sequence comprises a genetic construct having genes encoding for multiple Mycobacterial major extracellular proteins wherein said genes encoding for said Mycobacterial major extracellular proteins are orientated in the same direction relative to each other within the genetic construct.

19. The immunogenic composition according to claim 15 wherein said extrachromosomal nucleic acid sequence comprises a genetic construct having genes encoding for multiple Mycobacterial major extracellular proteins wherein said genes encoding for said Mycobacterial major extracellular proteins are orientated in opposite directions relative to each other within the genetic construct.

20. The immunogenic compositions according to any one of claims 15–19 wherein said Mycobacterial major extracellular proteins are from a species of *Mycrobacterium* selected from the group consisting of *Mycobacterium tuberculosis* (Mtb), *Mycobacterium bovis* (MB), and *Mycobacterium leprae* (ML).

21. An immunogenic composition comprising:

a growth regulatable recombinant BCG having an extrachromosomal nucleic acid sequence comprising a gene encoding for *Mycobacterium tuberculosis* 23.5 kDa major extracellular protein wherein said 23.5 kDa major extracellular protein is over expressed and secreted such that an immune response is induced in a mammal.

22. An immunogenic composition comprising:

a growth regulatable recombinant BCG having an extrachromosomal nucleic acid sequence comprising a gene encoding for *Mycobacterium tuberculosis* 30 kDa major extracellular protein wherein said 30 kDa major extracellular protein is over expressed and secreted such that an immune response is induced in a mammal.

23. An immunogenic composition comprising:

a growth regulatable recombinant BCG having an extrachromosomal nucleic acid sequence comprising a gene encoding for *Mycobacterium tuberculosis* 32A kDa major extracellular non-fusion protein wherein said 32A kDa major extracellular non-fusion protein is over expressed and secreted such that an immune response is induced in a mammal.

24. An immunogenic composition comprising:

a growth regulatable recombinant Bacille Calmette-Guérin (BCG) having an extrachromosomal nucleic acid sequence comprising a genetic construct having at least one gene encoding for a *Mycobacterium tuberculosis* (Mtb) 30 kDa major extracellular protein and an Mtb 23.5 kDa major extracellular non-fusion protein, wherein said Mtb 30 kDa major extracellular protein and said Mtb 23.5 kDa major extracellular non-fusion protein are over expressed and secreted.

25. An immunogenic composition comprising:

a growth regulatable recombinant BCG having an extrachromosomal nucleic acid sequence comprising a genetic construct having at least one gene encoding for a *Mycobacterium tuberculosis* (Mtb) 30 kDa major extracellular protein and an Mtb 23.5 kDa major extracellular protein, wherein said Mtb 30 kDa major extracellular protein and said Mtb 23.5 kDa major extracellular protein are over expressed and secreted such that an immune response is induced in a mammal.

26. An immunogenic composition comprising:

a growth regulatable recombinant BCG having an extrachromosomal nucleic acid sequence comprising a gene encoding for *Mycobacterium bovis* 30 kDa major extracellular protein under the control of a promoter wherein said 30 kDa major extracellular protein is over expressed and secreted such that an immune response is induced in a mammal.

27. An immunogenic composition comprising:

a growth regulatable recombinant BCG having an extrachromosomal nucleic acid sequence comprising a gene encoding for *Mycobacterium leprae* 30 kDa major extracellular protein under the control of a promoter wherein said 30 kDa major extracellular protein is over expressed and secreted such that an immune response is induced in a mammal.

28. An immunogenic composition comprising:

a growth regulatable recombinant BCG having an extrachromosomal nucleic acid comprising a gene encoding for *Mycobacterium leprae* 30 kDa major extracellular protein under the control of a promoter wherein said *Mycobacterium leprae* 30 kDa major extracellular protein is over expressed and secreted from said recombinant BCG such that both a humoral and a cellular immune response is induced in a mammal.

29. An immunogenic composition comprising:

a growth regulatable recombinant Bacille Calmette-Guérin (BCG) having an extrachromosomal nucleic acid sequence comprising a genetic construct having at least one gene encoding for a *Mycobacterium tuberculosis* (Mtb) 30 kDa major extracellular protein and an Mtb 23.5 kDa major extracellular protein, wherein said Mtb 30 kDa major extracellular protein and said Mtb 23.5 kDa major extracellular protein are over expressed and secreted;

and wherein said genetic construct comprises a gene encoding for said Mtb 23.5 kDa protein and a gene encoding for said Mtb 30 kDa protein and wherein said genes are orientated in the same direction relative to each other within said genetic construct.

30. An immunogenic composition comprising:

a growth regulatable recombinant Bacille Calmette-Guérin (BCG) having an extrachromosomal nucleic acid sequence comprising a genetic construct having at least one gene encoding for a *Mycobacterium tuberculosis* (Mtb) 30 kDa major extracellular protein and an Mtb 23.5 kDa major extracellular protein, wherein said Mtb 30 kDa major extracellular protein and said Mtb 23.5 kDa major extracellular protein are over expressed and secreted;

and wherein said genetic construct comprises a gene encoding for said Mtb 23.5 kDa protein and a gene encoding for said Mtb 30 kDa protein and wherein said genes are orientated in opposite directions relative to each other within said genetic construct.

31. The immunogenic composition according to any one of claims 15, 21, 22 or 23 wherein said growth regulatable recombinant BCG is an auxotroph and wherein tryptophan or glutamine is used to regulate growth of said auxotroph.

32. The immunogenic composition according to any one of claims 15, 21, 22, 25, 26, 27 or 28, wherein said immune response is a protective immune response.

33. The immunogenic composition according to any one of claims 7, 8, 10, 11, 21, 22 or 23 wherein said mammal is a human.

34. An immunogenic composition comprising a growth regulatable recombinant Bacille Calmette-Guérin (BCG) having an extrachromosomal nucleic acid sequence comprising a genetic construct having at least one gene encoding for a Mycobacterium major extracellular protein.

* * * * *